(12) United States Patent
Yamada et al.

(10) Patent No.: US 11,428,714 B2
(45) Date of Patent: Aug. 30, 2022

(54) SENSOR DEVICE, WATER AMOUNT MEASUREMENT DEVICE, WATER AMOUNT MEASUREMENT METHOD, INFORMATION PROCESSING DEVICE, AND INFORMATION PROCESSING METHOD

(71) Applicants: SONY CORPORATION, Tokyo (JP); SONY SEMICONDUCTOR SOLUTIONS CORPORATION, Kanagawa (JP)

(72) Inventors: Atsushi Yamada, Kanagawa (JP); Kyohei Yoshimitsu, Tokyo (JP); Hiroyuki Mita, Saitama (JP); Sachio Iida, Kanagawa (JP); Seiji Kobayashi, Kanagawa (JP); Toshiyuki Hiroi, Tokyo (JP)

(73) Assignees: Sony Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 289 days.

(21) Appl. No.: 16/616,608

(22) PCT Filed: Apr. 18, 2018

(86) PCT No.: PCT/JP2018/016007
§ 371 (c)(1),
(2) Date: Nov. 25, 2019

(87) PCT Pub. No.: WO2018/221051
PCT Pub. Date: Dec. 6, 2018

(65) Prior Publication Data
US 2020/0182906 A1    Jun. 11, 2020

(30) Foreign Application Priority Data

Jun. 2, 2017   (JP) .............................. JP2017-109917

(51) Int. Cl.
*G01R 1/04*    (2006.01)
*G01R 1/067*   (2006.01)
(Continued)

(52) U.S. Cl.
CPC ......... *G01R 1/07307* (2013.01); *G01N 22/04* (2013.01); *G01R 1/06772* (2013.01)

(58) Field of Classification Search
CPC .......... G01R 1/04; G01R 1/067; G01R 1/073; G01R 27/04; G01R 27/32; G01N 22/04
See application file for complete search history.

(56) References Cited

U.S. PATENT DOCUMENTS

2004/0164746 A1   8/2004  Anderson et al.
2005/0017735 A1*  1/2005  Cariou et al. .......... G01R 27/04
2010/0295556 A1  11/2010  Richter

FOREIGN PATENT DOCUMENTS

CN    101799436 A    8/2010
CN    102680521 A    9/2012
(Continued)

OTHER PUBLICATIONS

International Search Report prepared by the Japan Patent Office dated Jun. 27, 2018, for International Application No. PCT/JP2018/016007.

*Primary Examiner* — Neel D Shah
(74) *Attorney, Agent, or Firm* — Sheridan Ross P.C.

(57) ABSTRACT

A sensor device according to an embodiment of the present technology includes a sensor head and a measurement unit. The sensor head includes a first probe and a second probe, the first probe including a first antenna section used for transmission, the second probe including a second antenna section used for reception, the second probe being situated at a specified distance from the first probe and facing the first probe. The measurement unit includes a signal generator that generates a measurement signal that includes information (Continued)

regarding characteristics of a propagation of an electromagnetic wave in a medium between the first and second antenna sections.

21 Claims, 20 Drawing Sheets

(51) Int. Cl.
*G01R 1/073* (2006.01)
*G01R 27/04* (2006.01)
*G01N 22/04* (2006.01)

(56) References Cited

FOREIGN PATENT DOCUMENTS

| | | |
|---|---|---|
| JP | H10-090201 | 4/1998 |
| JP | H11-173998 | 7/1999 |
| JP | 2011-027664 | 2/2011 |
| JP | 2012-194027 | 10/2012 |

\* cited by examiner

SENSOR DEVICE, WATER AMOUNT MEASUREMENT DEVICE, WATER AMOUNT MEASUREMENT METHOD, INFORMATION PROCESSING DEVICE, AND INFORMATION PROCESSING METHOD

CROSS REFERENCE TO RELATED APPLICATIONS

This application is a national stage application under 35 U.S.C. 371 and claims the benefit of PCT Application No. PCT/JP2018/016007 having an international filing date of 18 Apr. 2018, which designated the United States, which PCT application claimed the benefit of Japanese Patent Application No. 2017-109917 filed 2 Jun. 2017, the entire disclosures of each of which are incorporated herein by reference.

TECHNICAL FIELD

The present technology relates to a sensor device, a water amount measurement device, a water amount measurement method, an information processing device, and an information processing method that are used for measuring a water amount in a medium such as soil.

BACKGROUND ART

Time-domain reflectometry (TDR) is known as a method for measuring a water amount in a medium. This method includes transmitting an electromagnetic wave along a metallic probe embedded in a medium, and calculating a water amount in the medium from relative permittivity measured using its reflection response (for example, refer to Patent Literature 1).

CITATION LIST

Patent Literature

Patent Literature 1: Japanese Patent Application Laid-open No. H10-90201

DISCLOSURE OF INVENTION

Technical Problem

However, there is a problem in which, since the TDR measures relative permittivity using the characteristics of a propagation of an electromagnetic wave in the vicinity of a probe in a medium, a gap produced in the vicinity of the probe has a great impact on the measurement, and thus it is not possible to measure relative permittivity correctly.

In view of the circumstances described above, it is an object of the present technology to provide a sensor device, a water amount measurement device, a water amount measurement method, an information processing device, and an information processing method that make it possible to improve accuracy in the measurement of relative permittivity of a medium or a water amount in the medium.

Solution to Problem

A sensor device according to an embodiment of the present technology includes a sensor head and a measurement unit.

The sensor head includes a first probe and a second probe, the first probe including a first antenna section used for transmission, the second probe including a second antenna section used for reception, the second probe being situated at a specified distance from the first probe and facing the first probe.

The measurement unit includes a signal generator that generates a measurement signal that includes information regarding characteristics of a propagation of an electromagnetic wave in a medium between the first and second antenna sections.

The sensor device obtains the characteristics of a propagation of an electromagnetic wave in a medium between the first probe and the second probe that respectively perform transmission and reception of an electromagnetic wave. The impact that a gap produced in the vicinity of each probe has on the measurement of relative permittivity or a water amount, can be made small sufficiently to ignore, by making a distance between the first and second probes sufficiently larger than the gap.

The sensor device transmits and receives an electromagnetic wave through the first and second antenna sections, and this prevents the measurement accuracy from being decreased due to resonances of the probes.

The first and second probes may be each constituted of a coaxial cable that includes a core wire portion and a shield portion. In this case, the first and second antenna sections may be each configured as a hole provided in a portion of the shield portion.

This makes it possible to obtain a simple configuration of a probe including an antenna section.

The first and second probes may each include an end resistance that is electrically connected between an end of the core wire portion and the shield portion.

This prevents undesired reflections of a transmission signal and a reception signal at the ends of probes.

The sensor head may further include an electromagnetic wave absorption material. The electromagnetic wave absorption material is provided in each of the first and second probes to cover a portion around the hole in the shield portion.

This prevents a transmission signal and a reception signal from being leaked from a region other than the hole.

The electromagnetic wave absorption material may include ferrite.

The sensor head may further include a support substrate that includes a first arm, a second arm, and a coupling portion that couples the first arm to the second arm, and the first and second probes may be respectively constituted of striplines respectively provided in the first and second arms. This makes it possible to obtain a simple and tough configuration of the sensor head, and to improve the handleability.

In this case, the measurement unit may be mounted on the coupling portion.

This enables the sensor head and the measurement unit to be integral with each other.

The sensor head may further include a temperature detector. The temperature detector is provided in at least one of the first probe or the second probe and is capable of detecting a temperature of the medium.

This makes it possible to obtain information regarding a temperature of a medium that is used to correct measurement data.

The sensor head may further include an electric conductivity detector. The electric conductivity detector is provided in at least one of the first probe or the second probe and is capable of detecting electric conductivity of the medium.

This makes it possible to obtain information regarding electric conductivity of a medium that is used to correct measurement data.

The signal generator may include a signal creating section and a quadrature detector. The signal creating section inputs a pulse signal of a specified frequency to the first probe. The quadrature detector performs quadrature detection on an output from the second probe.

This makes it possible to generate information regarding a propagation delay time of an electromagnetic wave that propagates between probes.

The measurement unit may further include a communication section that is capable of transmitting the measurement signal to an information processing device.

This makes it possible to provide the measurement signal to the information processing device arranged in a location different from an observation point.

A water amount measurement device according to an embodiment of the present technology includes a sensor head, a measurement unit, and a signal processing section.

The sensor head includes a first probe and a second probe, the first probe including a first antenna section used for transmission, the second probe including a second antenna section used for reception, the second probe being situated at a specified distance from the first probe and facing the first probe.

The measurement unit generates a measurement signal that includes information regarding characteristics of a propagation of an electromagnetic wave in a medium between the first and second antenna sections.

The signal processing section measures a water amount in the medium using the measurement signal.

The signal processing section may include a delay time calculator, a relative permittivity calculator, and a water amount calculator. The delay time calculator calculates a propagation delay time of an electromagnetic wave between the first and second probes using the measurement signal. The relative permittivity calculator calculates relative permittivity of a medium using the propagation delay time. The water amount calculator calculates a water amount in the medium using the relative permittivity.

The sensor head may further include a temperature detector that is capable of detecting a temperature of the medium, and the signal processing section may be configured to correct the water amount according to an output from the temperature detector.

The sensor head may further include an electric conductivity detector that is capable of detecting electric conductivity of the medium, and the signal processing section may be configured to correct the water amount according to an output from the electric conductivity detector.

A water amount measurement method according to an embodiment of the present technology includes receiving, by a second antenna section of a second probe, an electromagnetic wave transmitted from a first antenna section of a first probe arranged in a medium, and generating a measurement signal that includes information regarding characteristics of a propagation of the electromagnetic wave, the second probe being arranged in the medium to be situated at a specified distance from the first probe. A water amount in the medium is measured using the measurement signal.

The measuring the water amount may include calculating a propagation delay time of the electromagnetic wave that is measured using the measurement signal, calculating relative permittivity of the medium using the propagation delay time, and calculating a water amount in the medium using the relative permittivity.

The medium may be soil.

An information processing device according to an embodiment of the present technology includes a delay time calculator, a relative permittivity calculator, and a water amount calculator.

The delay time calculator calculates a propagation delay time of an electromagnetic wave between a first probe and a second probe using an electromagnetic wave transmitted from a first antenna section of the first probe and received by a second antenna section of the second probe, the first probe being arranged in a medium, the second probe being arranged in the medium to be situated at a specified distance from the first probe.

The relative permittivity calculator calculates relative permittivity of the medium using the propagation delay time.

The water amount calculator calculates a water amount in the medium using the relative permittivity.

An information processing method according to an embodiment of the present technology includes calculating a propagation delay time of an electromagnetic wave between a first probe and a second probe using an electromagnetic wave transmitted from a first antenna section of the first probe and received by a second antenna section of the second probe, the first probe being arranged in a medium, the second probe being arranged in the medium to be situated at a specified distance from the first probe.

Relative permittivity of the medium is calculated using the propagation delay time.

A water amount in the medium is calculated using the relative permittivity.

Advantageous Effects of Invention

As described above, the present technology makes it possible to improve accuracy in the measurement of relative permittivity of a medium or a water amount in the medium.

Note that the effect described here is not necessarily limitative and may be any effect described in the present disclosure.

MODE(S) FOR CARRYING OUT THE INVENTION

Embodiments according to the present technology will now be described below with reference to the drawings.

First Embodiment

Figure 1:
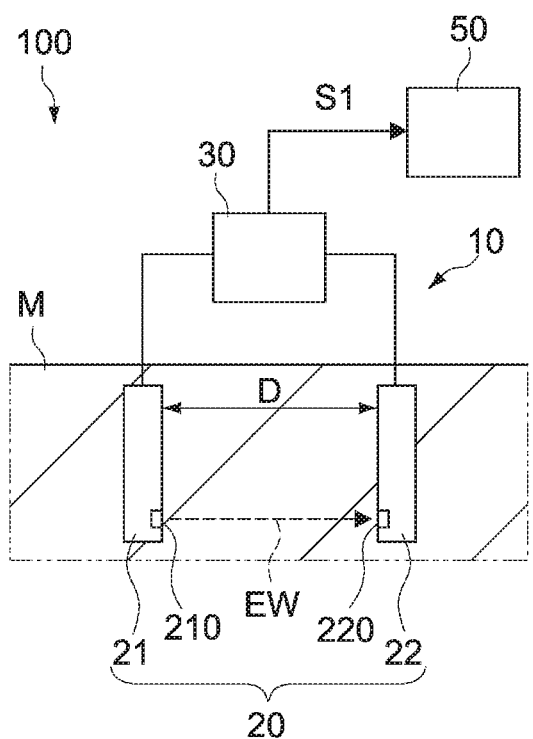
FIG. 1 schematically illustrates a configuration of a water amount measurement device that includes a sensor device according to a first embodiment of the present technology.
Figure 2:
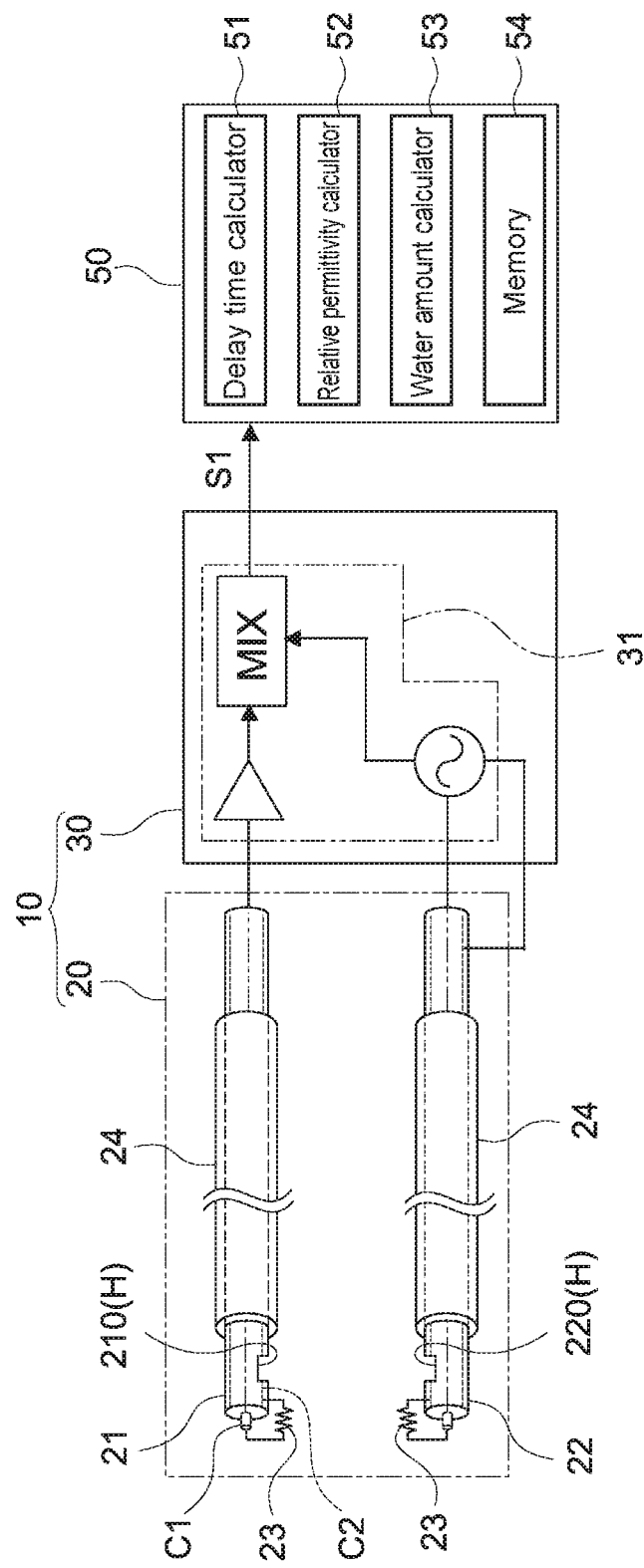
FIG. 2 is a block diagram illustrating a configuration of the water amount measurement device.

FIG. 1 schematically illustrates a configuration of a water amount measurement device that includes a sensor device according to an embodiment of the present technology. FIG. 2 is a block diagram illustrating a configuration of the water amount measurement device.

[Water Amount Measurement Device]

A water amount measurement device 100 of the present embodiment includes a sensor device 10 and a signal processing unit 50. In the present embodiment, an example of applying the present technology to the measurement of a water amount in soil where crops will grow, is described.

The sensor device 10 obtains the characteristics of a propagation of an electromagnetic wave in a medium (soil) M, and generates a measurement signal S1 used to calculate relative permittivity of the medium M. The signal processing unit 50 receives the measurement signal S1 from the sensor device 10, and calculates a water amount in the medium M using the measurement signal S1.

Each component is described in detail below.

The sensor device 10 includes a sensor head 20 and a measurement unit 30.

(Sensor Head)

The sensor head 20 includes a transmission probe 21 (a first probe) and a reception probe 22 (a second probe). The sensor head 20 respectively includes antenna sections 210 and 220 (a first antenna section and a second antenna section) that are arranged in a medium M such as soil and make it possible to transmit and receive an electromagnetic wave EW of a specified frequency between the transmission probe 21 and the reception probe 22.

The transmission probe 21 and the reception probe 22 are embedded in the medium M in a generally vertical pose such that they are situated at a distance D from each other and face each other. The transmission probe 21 and the reception probe 22 are each constituted of a coaxial cable that includes a core wire portion C1 and a shield portion C2. The thickness and the length of the cable are not particularly limited, and the cable may have an arbitrary thickness and an arbitrary length. For example, the cable can be easily inserted into soil if it has a thickness (a diameter) of 2 mm to 6 mm. The core wire portion C1 is constituted of a copper wire, and the shield portion C2 is constituted of a copper pipe, but the shield portion C2 may be constituted of a mesh made of copper wires. The outer surface of the shield portion C2 is not illustrated, but is covered with a protection layer constituted of an insulating material.

The transmission probe 21 is connected to an output terminal 34 of the measurement unit 30 (refer to FIG. 3), and transmits a transmission signal from the measurement unit 30 to the antenna section 210. The antenna section 210 is provided on a tip (an end) of the transmission probe 21 or near the tip of the transmission probe 21, and transmits an electromagnetic wave EW corresponding to the transmission signal to the reception probe 22.

The reception probe 22 is connected to an input terminal 35 of the measurement unit 30 (refer to FIG. 3), receives the electromagnetic wave EW using the antenna section 220, and inputs the reception signal to the measurement unit 30. The antenna section 220 is provided on a tip (an end) of the transmission probe 22 or near the tip of the transmission probe 22 such that the antenna section 220 faces the antenna section 210 of the transmission probe 21. The antenna sections 210 and 220 are not limited to respectively being provided on the tips of the probes 21 and 22, and may be respectively provided arbitrary positions such as central positions of the probes 21 and 22.

The antenna sections 210 and 220 are used to locally transmit and receive an electromagnetic wave EW at respective specified positions of the probes 21 and 22, and, typically, the antenna sections 210 and 220 are each constituted of a tiny antenna, the tiny antennas of the antenna sections 210 and 220 being formed to be sufficiently small in size to not resonate the respective probes 21 and 22. This makes it possible to prevent the measurement accuracy from being decreased due to resonances of the probes 21 and 22.

In the present embodiment, the antenna sections 210 and 220 each include a hole H provided in a portion of the shield portion C2. In other words, the probes 21 and 22 are each constituted of a leakage coaxial antenna, the leakage coaxial antennas of the antenna sections 210 and 220 respectively including the antenna sections 210 and 220 as radio wave leaking sections.

The hole H has an opening shape such as rectangle, circle, ellipse, or oval, and in the present embodiment, the hole H is formed to have an oval shape, the oval shapes of the holes H the antenna sections 210 and 220 respectively having long axes in longitudinal directions of the probes 21 and 22. The long axis of the hole H can be set as appropriate according to the wavelength of an electromagnetic wave EW to be used. For example, when the wavelength of the electromagnetic wave EW is 500 MHz to 8 GHz, the length of the long axis of the hole H is about 5 mm to 15 mm.

The transmission probe 21 and the reception probe 22 each include an end resistance 23. The end resistance 23 is electrically connected between an end of the core wire portion C1 and the shield portion C2. This prevents undesired reflections of a transmission signal and a reception signal at the ends of probes.

It is favorable that the tips of the transmission probe 21 and the reception probe 22 be covered with an electromagnetic-wave-permeability protection member (illustration omitted) that covers the antenna sections 210 and 220.

The transmission probe 21 and the reception probe 22 each further include a sleeve 24 that contains an electromagnetic wave absorption material. The sleeve 24 covers outer peripheries around the antenna sections 210 and 220 (the holes H) of the probes 21 and 22, and prevents a transmission signal and a reception signal from being leaked from a region other than the hole H.

Ferrite is primarily used as the electromagnetic wave absorption material constituting the sleeve 24, but it is not limited to this, and any other high permeability material such as sendust or permalloy may be used according to, for example, a frequency of the electromagnetic wave EW. The sleeve 24 may be omitted as necessary, or may be provided only in one of the probes 21 and 22.

The size of the distance D between the transmission probe 21 and the reception probe 22 is not particularly limited, and is, for example, from 20 mm to 100 mm. If the distance D is longer than 100 mm, there is an increase in the attenuation of the electromagnetic wave EW propagating through the medium M, which may result in being unable to obtain a sufficient reception intensity. On the other hand, if the distance D is shorter than 20 mm, there is a technical difficulty in performing observation. Further, if the distance D is shorter, a gap formed in the vicinity of the probe 21, 22 has a great impact, which may result in being unable to measure relative permittivity or a water amount correctly.

The gap is an air space formed between the medium M and a portion around the probe 21, 22, and is formed when the probe 21, 22 is embedded in the medium M from its surface, or when the probe 21, 22 is moved in the medium M. As described later, it is favorable that the size of a gap (the thickness of an air space) be smaller in order to measure relative permittivity of the medium M or a water amount in the medium M with a high degree of accuracy, but a gap of about 1 mm may typically be produced.

(Measurement Unit)

Figure 3:
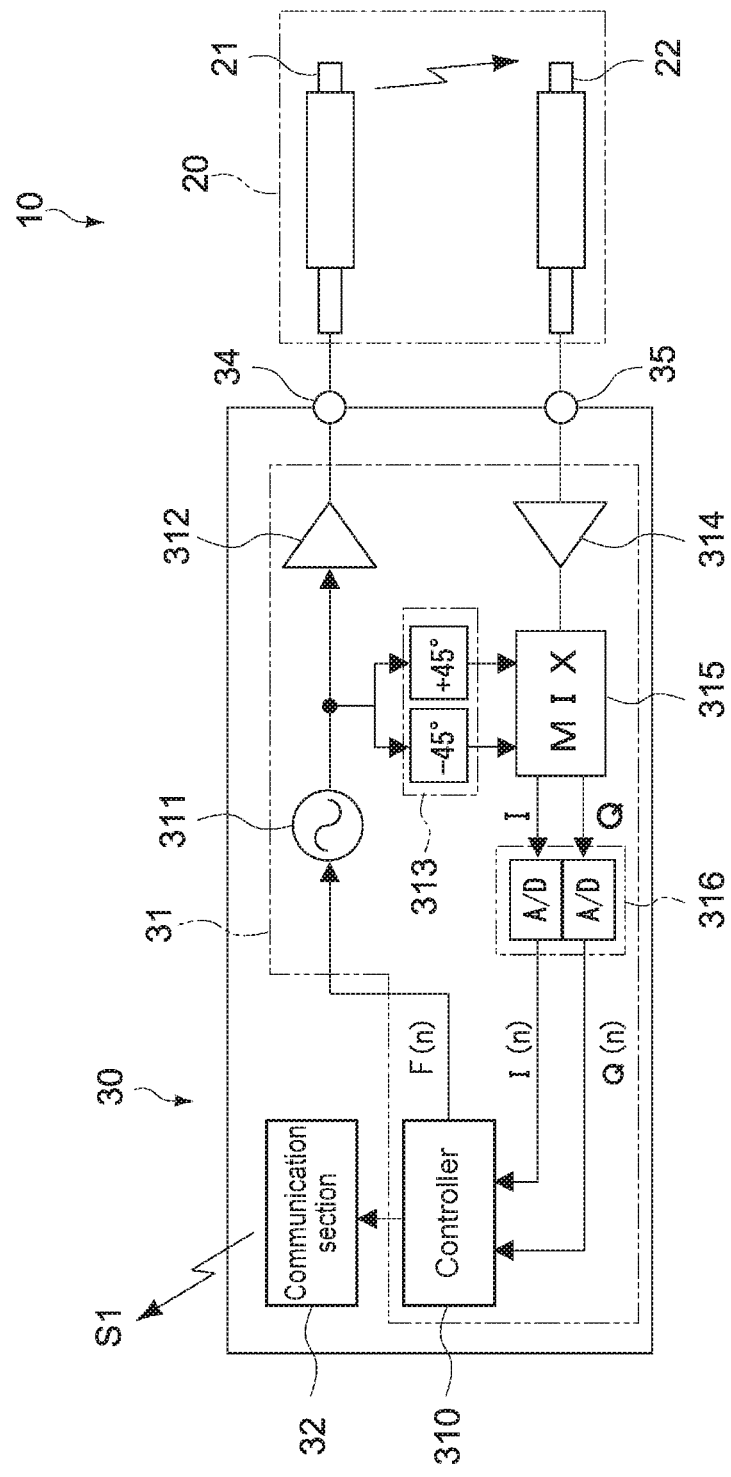
FIG. 3 is a block diagram illustrating a configuration of a measurement unit in the water amount measurement device.

FIG. 3 is a block diagram illustrating a configuration of the measurement unit 30.

The measurement unit 30 includes a signal generator 31 and a communication section 32. Typically, the measurement unit 30 is constituted of a network analyzer.

The signal generator 31 includes, for example, a controller 310, a signal creating section 311, a phase shifter 313, and a mixer 315. The signal generator 31 generates a measurement signal S1 that includes information regarding the characteristics of a propagation of the electromagnetic wave EW in the medium M between the antenna sections 210 of the probe 21 and the antenna section 220 of the reception probe 22.

The controller 310 is constituted of a computer that includes, for example, a central processing unit (CPU) and a memory, and controls components of the measurement unit 30, including the signal creating section 311 and the communication section 32.

The signal creating section 311 creates a transmission signal F of a specified frequency, and inputs the transmission signal F to the transmission probe 21 through an amplifier 312 and an output terminal 34. The signal creating section 311 generates a pulse wave (a pulse signal) as the transmission signal F, but may be configured to generate a continuous wave as the transmission signal F.

The signal creating section 311 may have a function that sweeps a frequency of the transmission signal F. In this case, the signal creating section 311 generates a transmission signal F of, for example, 500 MHz to 8 GHz according to an instruction given by the controller 310.

The phase shifter 313 separates the transmission signal F into two signals whose respective phases are shifted by 90 degrees from each other, and inputs the two signals to the mixer 315. The mixer 315 mixes a reception signal with the two signals output from the phase shifter 313 to modulate those signals into two response signals (I signal/Q signal), the reception signal being input from the reception probe 22 through the input terminal 35 and an amplifier 314, the two response signals being orthogonal to each other. These response signals are converted into a digital signal from an analog signal through an AD converter 316, so as to be generated as the measurement signal S1 in the controller 310.

The phase shifter 313 and the mixer 315 constitute a quadrature detector that performs quadrature detection (IQ detection) on an output from the reception probe 22. The sum of squares of the I signal and the Q signal corresponds to the intensity of the reception signal, the square root of the sum of squares of the I signal and the Q signal corresponds to the amplitude of the reception signal, and the arctangent of the I signal and the Q signal corresponds to a phase.

The communication section 32 is constituted of a communication module that includes an antenna for communication. The communication section 32 is used to wirelessly transmit the measurement signal S1 from the sensor device 10 to the signal processing unit 50. This makes it possible to provide the measurement signal S1 to the signal processing unit 50 arranged in a location different from an observation point. The configuration is not limited to this, and the sensor device 10 may be connected to the signal processing unit 50 through, for example, a distribution cable.

(Signal Processing Unit)

As illustrated in FIG. 2, the signal processing unit 50 includes a delay time calculator 51, a relative permittivity calculator 52 and a water amount calculator 53, and a memory 54. The signal processing unit 50 is constituted of an information processing device that measures a water amount in the medium M using the measurement signal S1 transmitted from the sensor device 10 (the measurement unit 30).

The information processing device may be provided by a hardware component, such as a CPU, a random access memory (RAM), or a read only memory (ROM), that is used in a computer, and by necessary software. Instead of, or in addition to the CPU, for example, programmable logic device (PLD) such as a field programmable gate array (FPGA), a digital signal processor (DSP), or an application specific integrated circuit (ASIC) may be used.

In the present embodiment, the delay time calculator 51, the relative permittivity calculator 52, and the water amount calculator 53 are configured as functional blocks by the CPU executing a specified program. The memory 54 is configured by, for example, the ROM of the signal processing unit 50. Of course, dedicated hardware such as an integrated circuit (IC) may be used in order to provide each block. A program is installed in the signal processing unit 50, for example, through various recording media.

Alternatively, a program may be installed through, for example, the Internet.

The delay time calculator 51 is configured to calculate, using the measurement signal S1, a propagation delay time of an electromagnetic wave EW between the transmission probe 21 (the antenna section 210) and the reception probe 22 (the antenna section 220).

The propagation delay time of an electromagnetic wave EW is typically a difference that the propagation time of the electromagnetic wave EW in a medium M has with the propagation time of an electromagnetic wave in air. A propagation delay time of an electromagnetic wave depends on the relative permittivity of a transmission path, and a propagation delay time is proportional to the square root of the relative permittivity of a medium. In general, the relative permittivity of soil itself is about 1 to 10, and varies depending on a water amount. Thus, this indicates that it will be possible to indirectly measure the water amount in the medium M if it is possible to measure a propagation delay time.

A method for calculating a propagation delay time is not particularly limited, and in the present embodiment, an inverse Fourier transform (IFFT) is performed on the measurement signal S1 to obtain an impulse response, and a pulse delay time is calculated from its peak position. The propagation delay time of the electromagnetic wave EW is calculated by subtracting transmission times (cable transmission times) of the probes 21 and 22 from the pulse delay time.

The relative permittivity calculator 52 is configured to calculate the relative permittivity of the medium M using the propagation delay time of the electromagnetic wave E that is calculated in the delay time calculator 51. The relative permittivity of water is typically 80.

The water amount calculator 53 is configured to calculate a water amount in the medium M using the relative permittivity calculated in the relative permittivity calculator 52. For example, the Topp's formula is used to calculate the water amount (described later), and water content by volume [%] in the medium M is calculated as the water amount.

The signal processing unit 50 may further include, for example, a communication section and a display section, the communication section being capable of communicating with the communication section 32 of the measurement unit 30, the display section being capable of displaying, for example, information regarding a propagation delay time, relative permittivity, and a water amount that are calculated in each functional block.

[Water Amount Measurement Method]

The signal processing unit 50 is described in detail below, together with a typical operation of the water amount measurement device according to the present embodiment.

Figure 4:
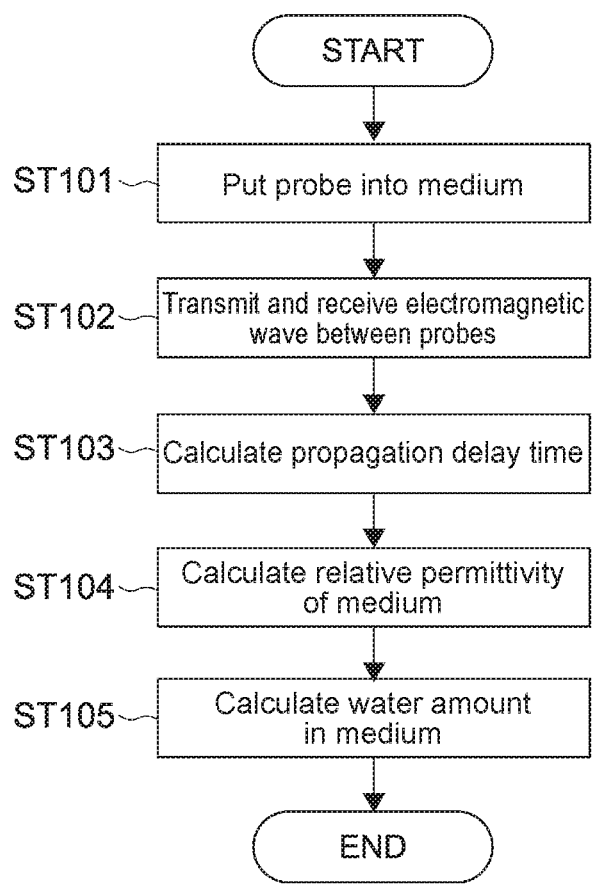
FIG. 4 is a flowchart of a water amount measurement method in an embodiment of the present technology.

FIG. 4 is a flowchart of a water amount measurement method in the present embodiment.

First, as illustrated in FIG. 1, the transmission probe 21 and the reception probe 22 are embedded in soil M (Step 101). The facing distance D between the transmission probe 21 and the reception probe 22 is, for example, 50 mm.

Next, an electromagnetic wave EW is transmitted and received between the transmission probe 21 (the antenna section 210) and a reception antenna (the antenna section 220) (Step 102).

In the present embodiment, the measurement unit 30 generates a measurement signal S1 while changing, in 10 MHz steps, a frequency of a transmission signal F(n) input to the transmission probe 21, the measurement signal S1 including orthogonal frequency response signals (I(n) signal and Q(n) signal) that are a reception signal output from the reception probe 22, and transmits the measurement signal S1 to the signal processing unit 50.

Next, the signal processing unit 50 (the delay time calculator 51) calculates, using the measurement signal S1, a propagation delay time of the electromagnetic wave EW between the transmission probe 21 and the reception probe 22 (Step 103).

The delay time calculator 51 performs an inverse Fourier transform on the reception signal using a fast Fourier transform (FFT) so as to obtain an impulse response h(i), where the I(n) signal is the real part and the Q(n) signal is the imaginary part.

$$h(\tau) = FFT\{I(n), Q(n)\} \quad (1)$$

The delay time calculator 51 obtains a pulse delay time τ [s] from the peak position of the impulse response h(τ), and subtracts a cable transmission time τ0 [s] from the pulse delay time τ, so as to obtain a propagation delay time $t_{delay}$ [s].

$$\tau_{delay} = \tau - \tau_0 \quad (2)$$

Next, the signal processing unit 50 (the relative permittivity calculator 52) calculates relative permittivity $\varepsilon_r$ of the medium M, where the propagation delay time is $\tau_{delay}$ [s], the light speed is c [m/s], and the distance (D) between probes is d [m] (Step 104).

$$\tau_{delay} = d \cdot \sqrt{(\varepsilon_r)}/c \quad (3)$$

Next, the signal processing unit 50 (the water amount calculator 53) calculates a water amount (water content by volume) θ [%] in the medium M using the Topp's formula.

$$\theta = -5.3 \times 10^{-2} + 2.92 \times 10^{-2} \varepsilon_r - 5.5 \times 10^{-4} \varepsilon_r^2 + 4.3 \times 10^{-6} \varepsilon_r^3 \quad (4)$$

As described above, the relative permittivity of the medium M and the water content by volume in the medium M are calculated.

In the present embodiment, the relative permittivity of the medium M and the water content by volume in the medium M are calculated using a propagation delay time of the electromagnetic wave EW between the transmission probe 21 and the reception probe 22 in the medium M. The distance D (50 mm) between the two probes 21 and 22 is much larger than a gap (1 mm) produced in the vicinity of each of the probes 21 and 22, and thus the impact those gaps have on the measurement of the relative permittivity is smaller. This results in preventing a measuring error from occurring due to a gap and in improving accuracy in the measurement of relative permittivity of the medium M and a water amount in the medium M.

Figure 5:
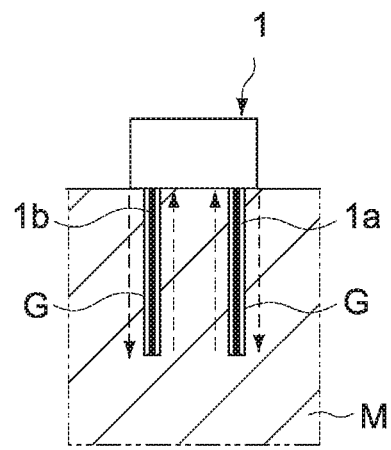
FIG. 5 is a schematic diagram explaining the TDR.

Here, as illustrated in FIG. 5, in the TDR, two measurement probes 1a and 1b of a TDR sensor 1 are embedded in a medium, a pulse signal (an electromagnetic wave) is input along these measurement probes, and a propagation delay time of an electromagnetic wave is calculated using reflection responses obtained at the ends of the probes. However, if there is a gap G around the probe 1a, 1b, information regarding the relative permittivity of the gap G will be included in a response signal, which results in being unable to measure the relative permittivity of the medium M correctly. Thus, in the TDR, the occurrence of a measuring error is greatly increased according to the size of a gap G.

Figure 6:
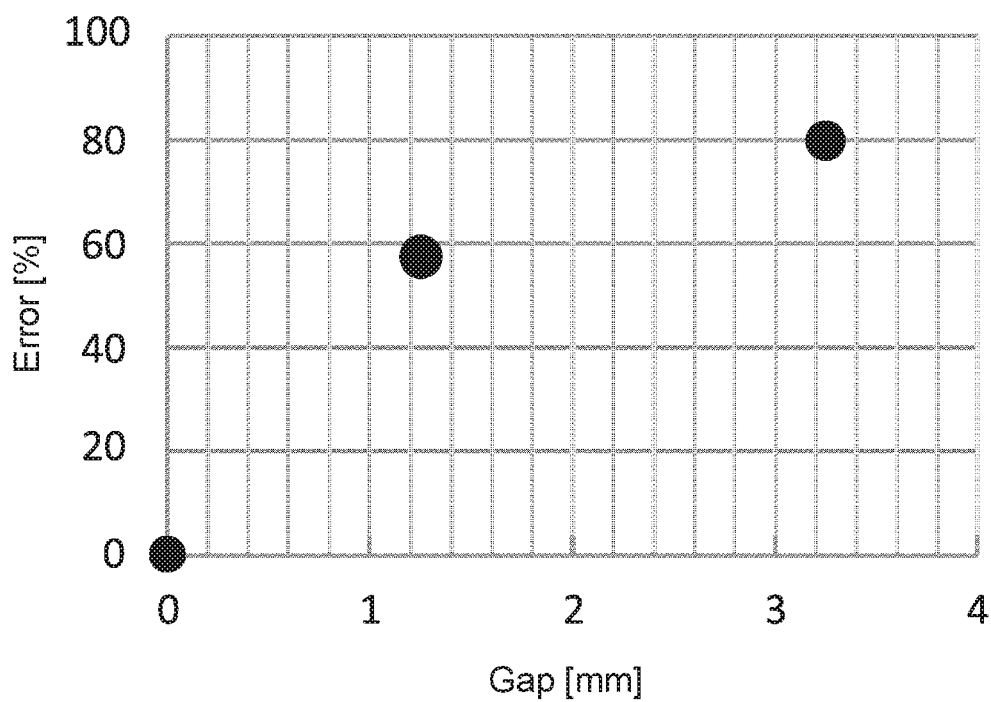
FIG. 6 illustrates an experimental result demonstrating an impact that a gap has on a measurement value obtained by the TDR.

FIG. 6 illustrates an example of an impact that a gap has on a measurement value obtained by the TDR. In the figure, the vertical axis represents an error between a measurement value obtained by the TDR and a measurement value obtained by a soil sampling method using the same soil, and the horizontal axis represents the size of a gap. The soil sampling method is a method for calculating a water amount in soil from weights before and after the soil is dried, and the measurement value is not affected by a gap. On the other hand, in the TDR, an impact that a gap has on the measurement value is too great to ignore, and a measurement value obtained by the TDR greatly differs from a measurement value obtained by the soil sampling method. Thus, in the TDR, the variation in measurement value depending on a worker is more likely to occur, and thus there is a need for a high level of proficiency to embed a measurement probe in a medium in order to prevent the occurrence of a gap as much as possible.

On the other hand, in the present embodiment, the characteristics of delay in propagation of an electromagnetic wave between the two probes 21 and 22 are evaluated, the two probes 21 and 22 being arranged in the medium M to be situated at a distance from each other, the distance being sufficiently larger than the gap, as described above. This makes it possible to calculate information regarding relative permittivity of the medium M with a high degree of accuracy without substantially being affected by a gap.

Figure 7:
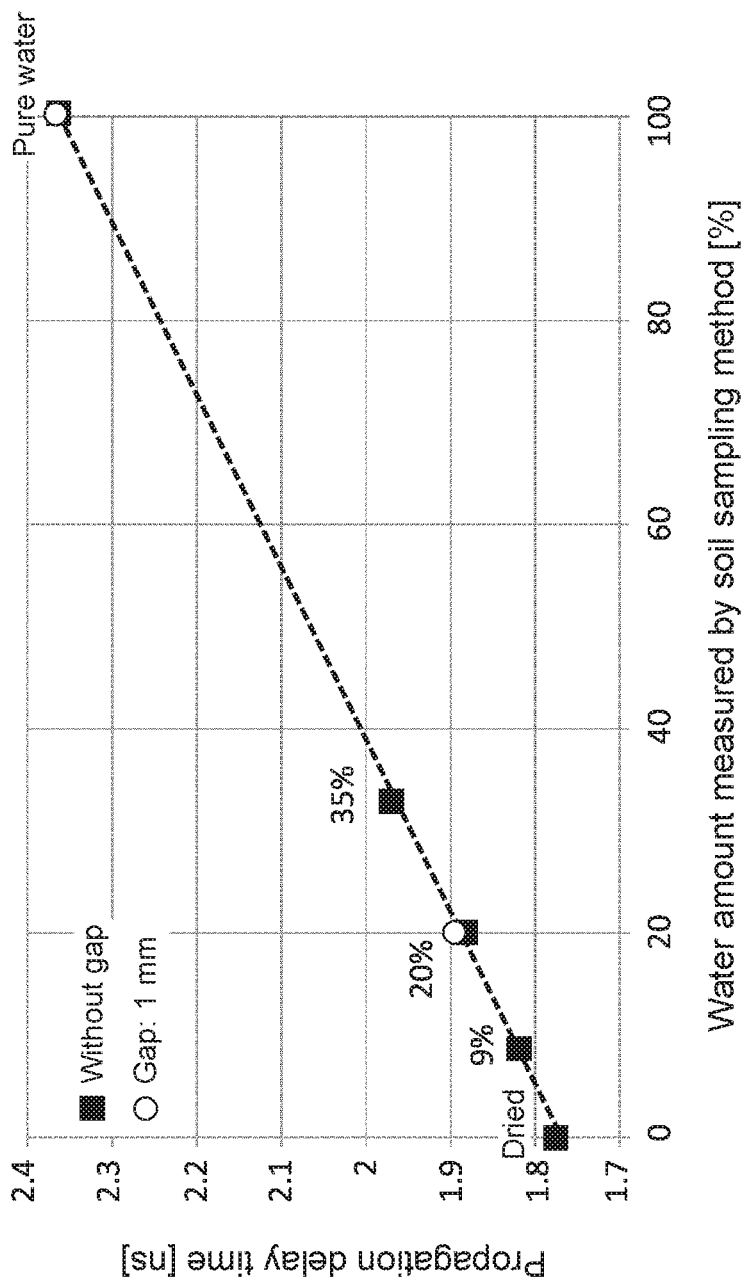
FIG. 7 illustrates an experimental result of comparing a measurement value obtained by the measurement method with a measurement value obtained by a soil sampling method.

FIG. 7 illustrates an experimental result of comparing a measurement value obtained according to the present embodiment with a measurement value obtained by a soil sampling method. In the figure, the vertical axis represents a propagation delay time of an electromagnetic wave that is base data for a water amount measured with respect to an arbitrary soil, and the horizontal axis represents a measurement value obtained by a soil sampling method with respect to the same soil. In the figure, the black square represents a measurement value without a gap, and the white circle represents a measurement value when there exists a gap of 1 mm.

As illustrated in FIG. 7, there is little error in measurement value between the present embodiment and the soil sampling method. Moreover, a steady measurement value is obtained regardless of the presence or absence of gap, so the variation in measurement value depending on a worker is less likely to occur, and thus there is no need for a high level of proficiency to put a probe into soil.

Figure 8:
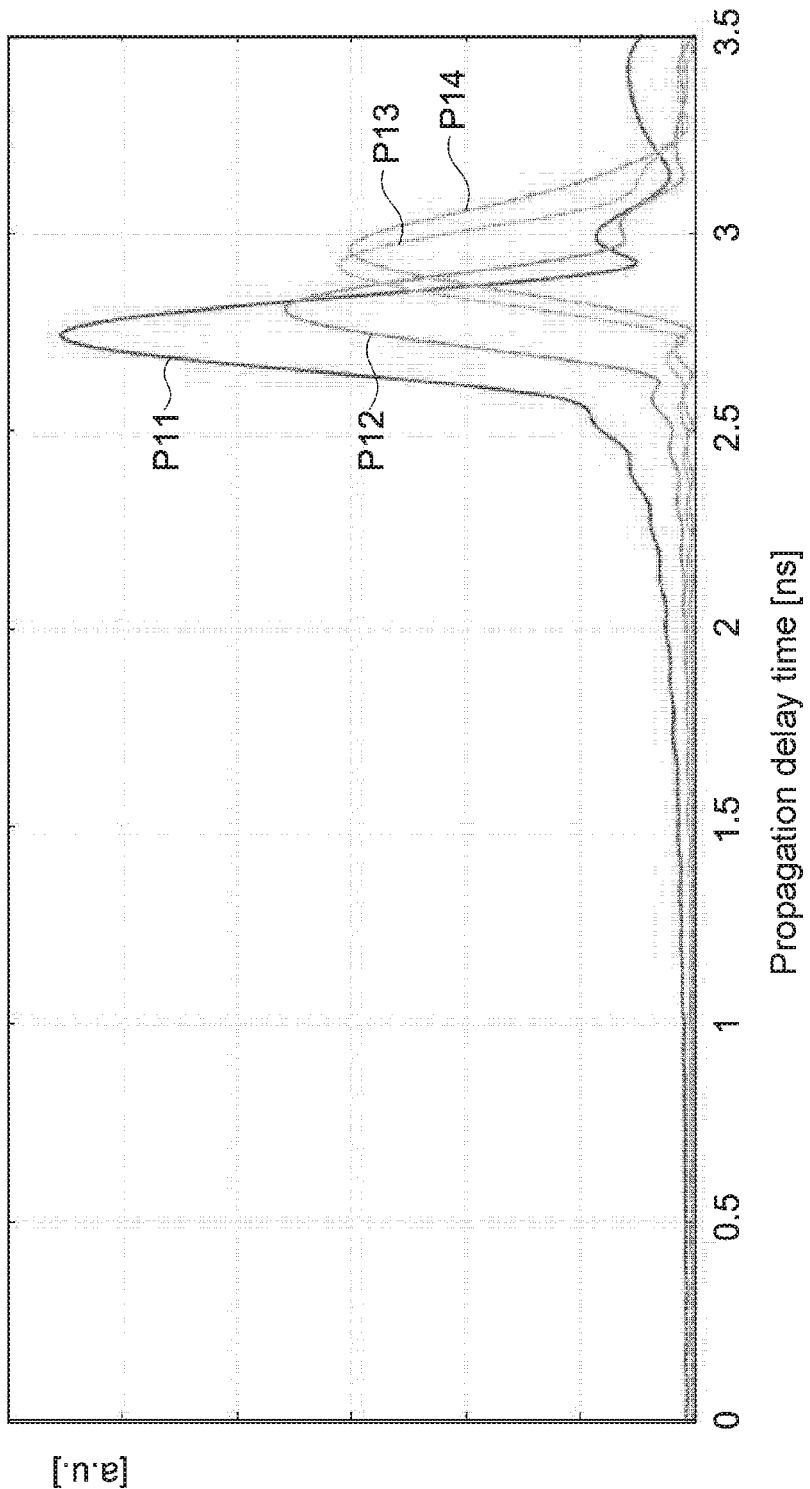
FIG. 8 is a diagram explaining an effect provided by the water amount measurement device.

Next, with respect to four types of soils whose water amounts (water content by volume) are different from one another, the propagation delay time of an electromagnetic wave (an impulse response) was measured by the water amount measurement method of the present embodiment described above. FIG. 8 illustrates a result of it. "Standard sand (Toyoura Standard Sand)" of Toyoura Keiseki Kogyo Co., Ltd. was used as soil. In FIG. 8, waveforms P11, P12, P13, and P14 respectively correspond to samples whose respective water contents by volume are 0%, 8%, 17%, and 25%. Values of relative permittivity that are calculated using the formula (4) described above, were 1.9, 5.0, 9.1, and 13.4, respectively.

Figure 9:
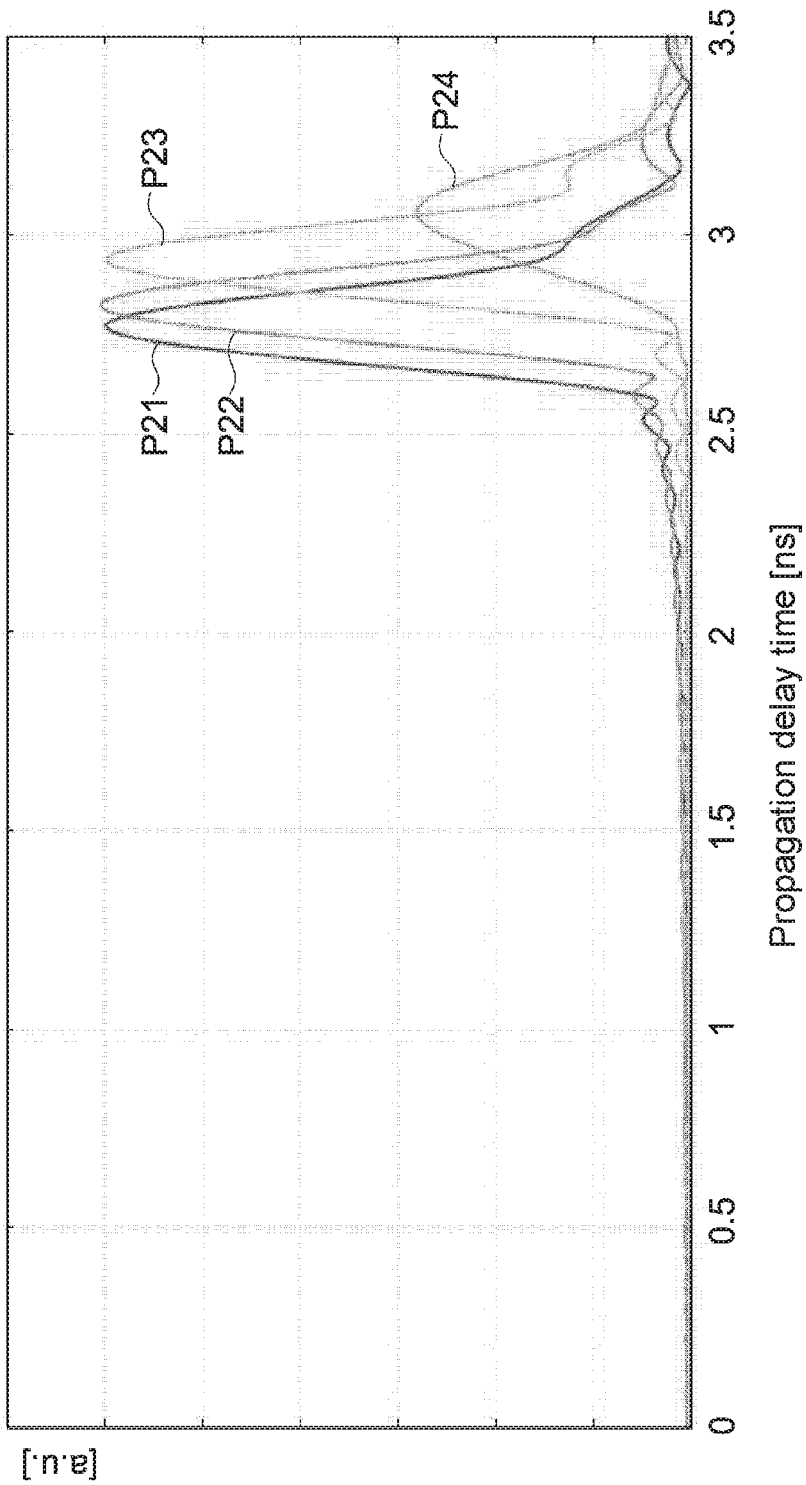
FIG. 9 is a diagram explaining an effect provided by the water amount measurement device.

FIG. 9 illustrates a result of an experiment that was performed in a similar way using organic soil ("culture soil for raising seedling" of TAKII & Co., Ltd) as soil. In FIG. 9, waveforms P21, P22, P23, and P24 respectively correspond to samples whose respective water contents by volume are 11%, 19%, 27%, and 36%. Values of relative permittivity that are calculated using the formula (4) described above, were 6.4, 10.3, 14.7, and 21.2, respectively.

With respect to a relationship between an impulse response and water content by volume, an approximation was determined, and comparison with water content by volume of the same delay time was performed, and a difference in soil (between standard sand and organic soil) was confirmed. As a result, there was an error of 7%. It is presumed that such an error was caused due to organic soil itself being less dense than standard sand, and due to the permittivity of soil itself being different.

Figure 10:
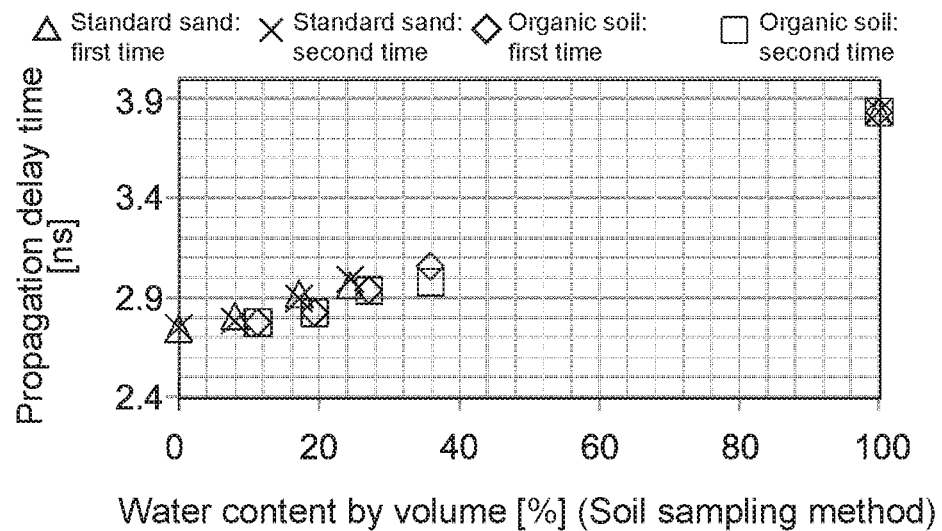
FIG. 10 is a diagram explaining an effect provided by the water amount measurement device.
Figure 11:
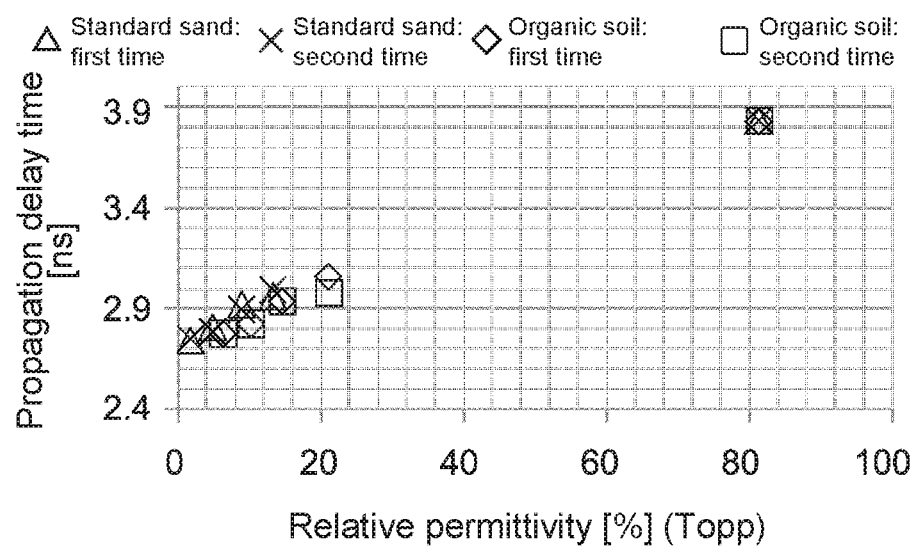
FIG. 11 is a diagram explaining an effect provided by the water amount measurement device.

FIG. 10 illustrates a graph plotted with the vertical axis representing a peak position of an impulse response (propagation delay time) and the horizontal axis representing water content by volume obtained by a soil sampling method. Likewise, FIG. 11 illustrates a graph plotted with the vertical axis representing a peak position of an impulse response and the horizontal axis representing relative permittivity calculated using the formula (4) described above. With respect to standard sand and organic soil, measurement was performed twice for each of the standard sand and the organic soil on the assumption of being affected by a gap, but an error was 1% or less, and thus a gap had little impact.

The present embodiment makes it possible to measure water content by volume in soil with a high degree of accuracy, and thus, for example, it is possible to properly determine whether it is soil suitable for growing crops. Further, it becomes possible to appropriately manage a water amount in soil.

Second Embodiment

Figure 12:
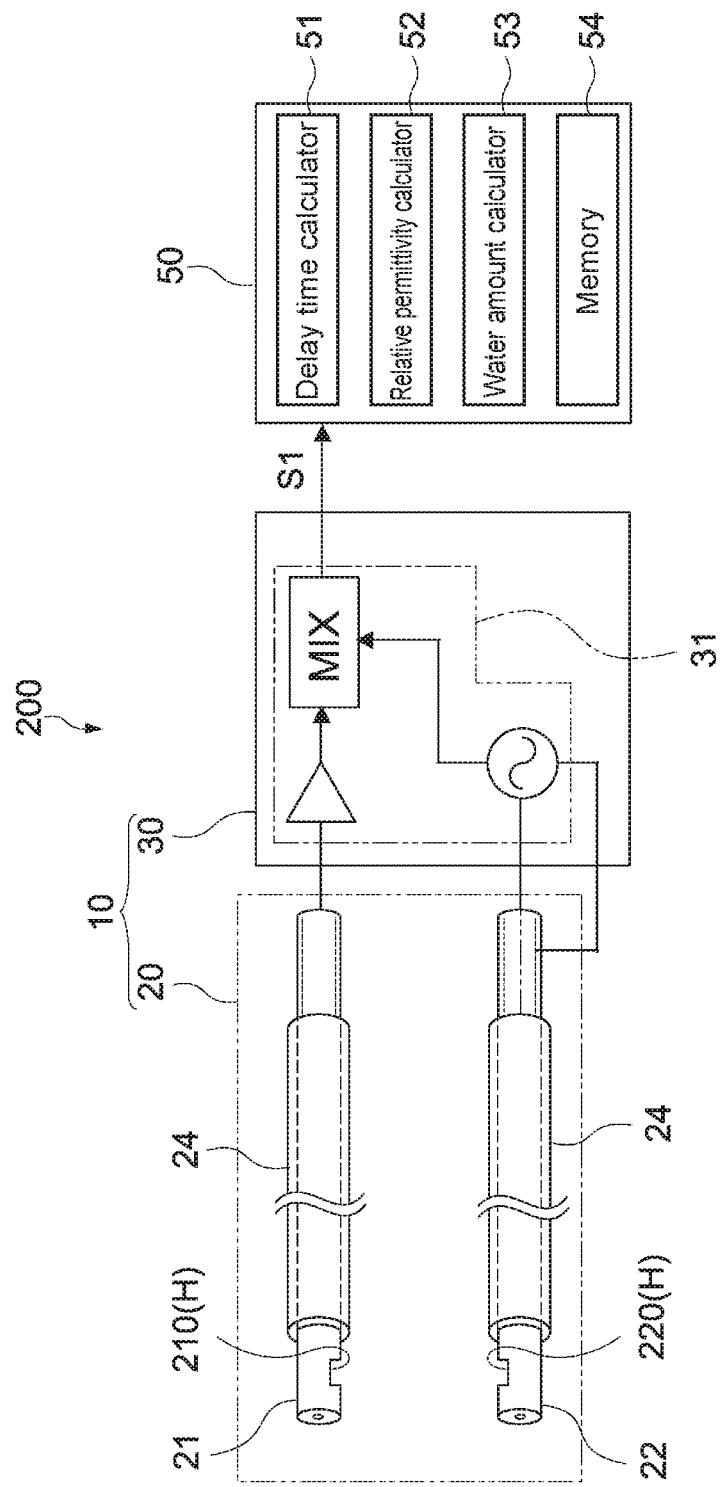
FIG. 12 schematically illustrates a configuration of a water amount measurement device that includes the sensor device according to a second embodiment of the present technology.

FIG. 12 schematically illustrates a configuration of a water amount measurement device according to a second embodiment of the present technology.

In the following descriptions, a component different from the first embodiment is primarily described, and the same component as the first embodiment is denoted by the same reference symbol and a description thereof is omitted or simplified.

A water amount measurement device 200 of the present embodiment is different from the water amount measurement device of the first embodiment in that the transmission probe 21 and the reception probe 22 constituting the sensor head 20 each do not include the end resistance 23 (refer to FIG. 2).

Figure 13:
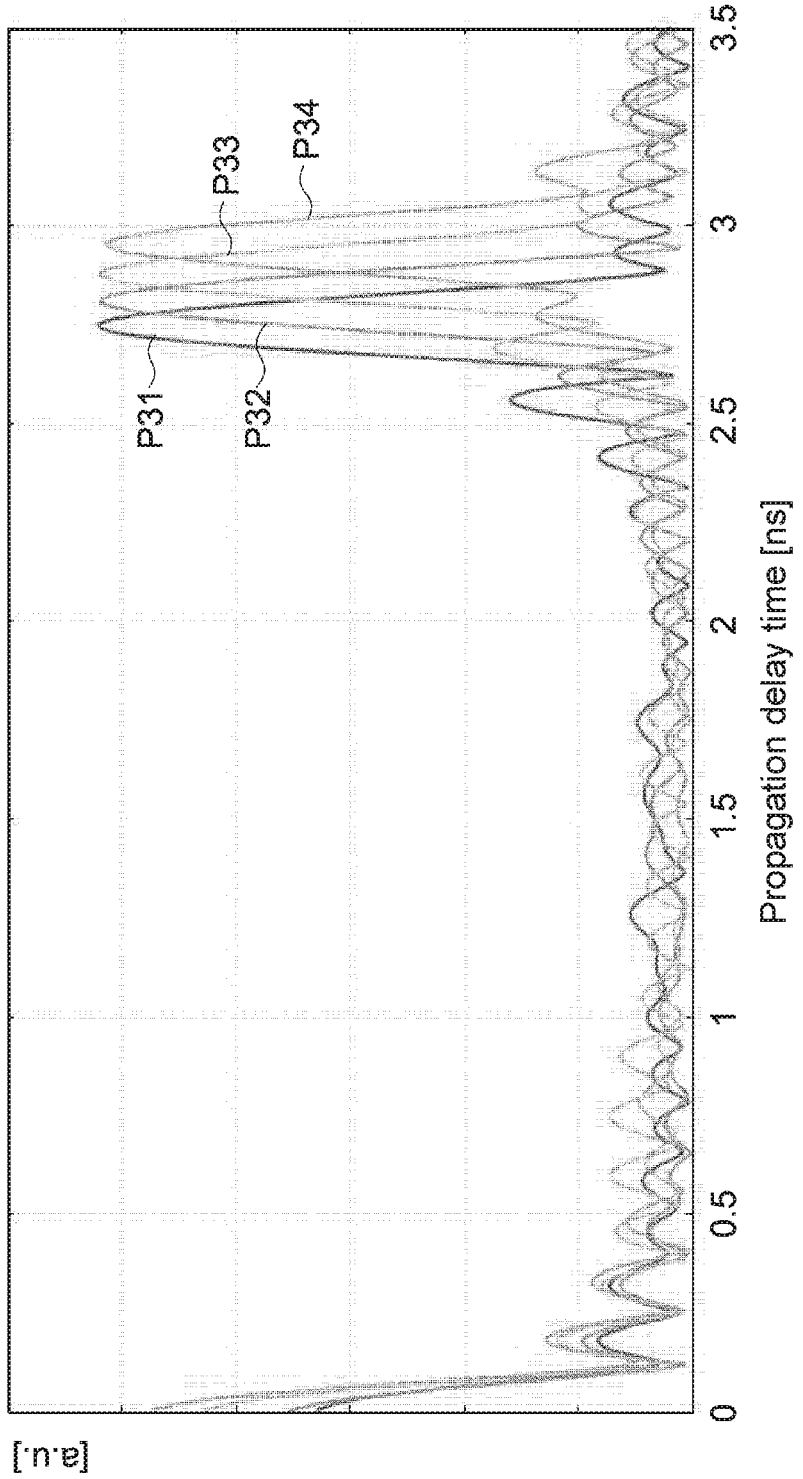
FIG. 13 is a diagram explaining an effect provided by the water amount measurement device.
Figure 14:
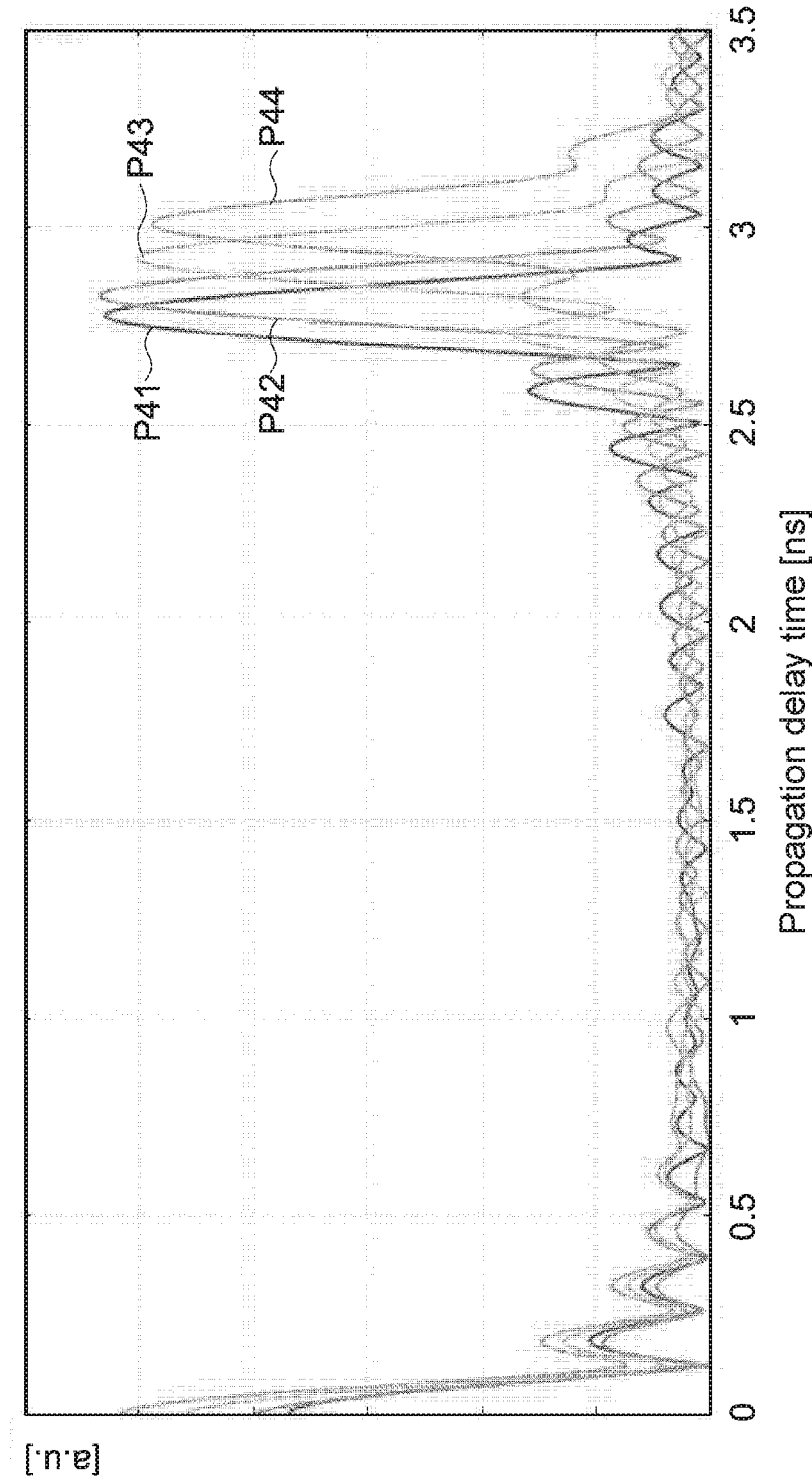
FIG. 14 is a diagram explaining an effect provided by the water amount measurement device.

The present embodiment also makes it possible to obtain an effect similar to that provided by the first embodiment described above. For example, FIG. 13 and FIG. 14 each illustrate the characteristics of a propagation of an electromagnetic wave that were measured with respect to the two types of soils (standard sand and organic soil) described in the first embodiment. In FIG. 13, waveforms P31, P32, P33, and P34 respectively correspond to samples of standard sand whose respective water contents by volume are 0%, 8%, 17%, and 25%. In FIG. 14, waveforms P41, P42, P43, and P44 respectively correspond to samples of organic soil whose respective water contents by volume are 11%, 19%, 27%, and 36%.

Further, it was confirmed that the omission of providing an end resistance results in improving electromagnetic wave permeability (sensitivity) and thus the propagation characteristics can be measured with a nearly uniform sensitivity regardless of water amount.

Figure 15:
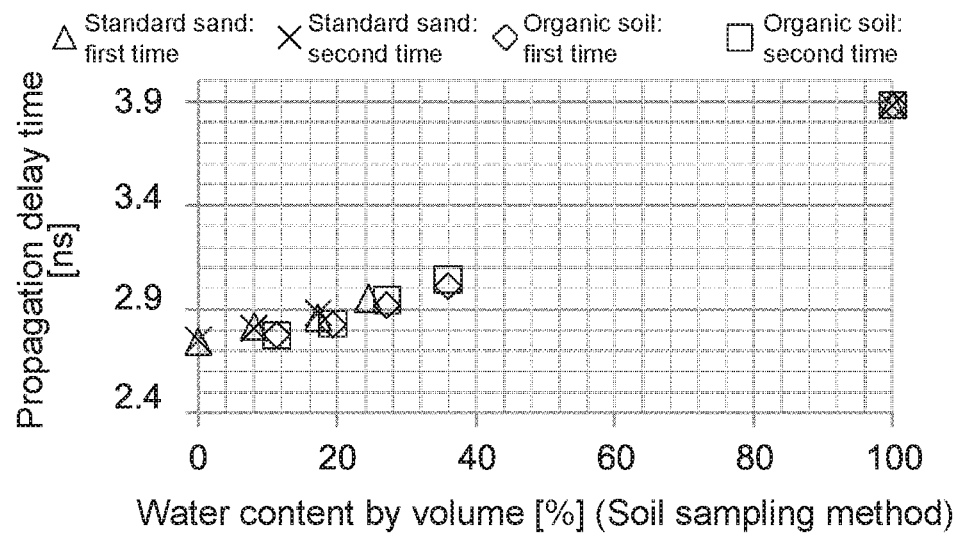
FIG. 15 is a diagram explaining an effect provided by the water amount measurement device.
Figure 16:
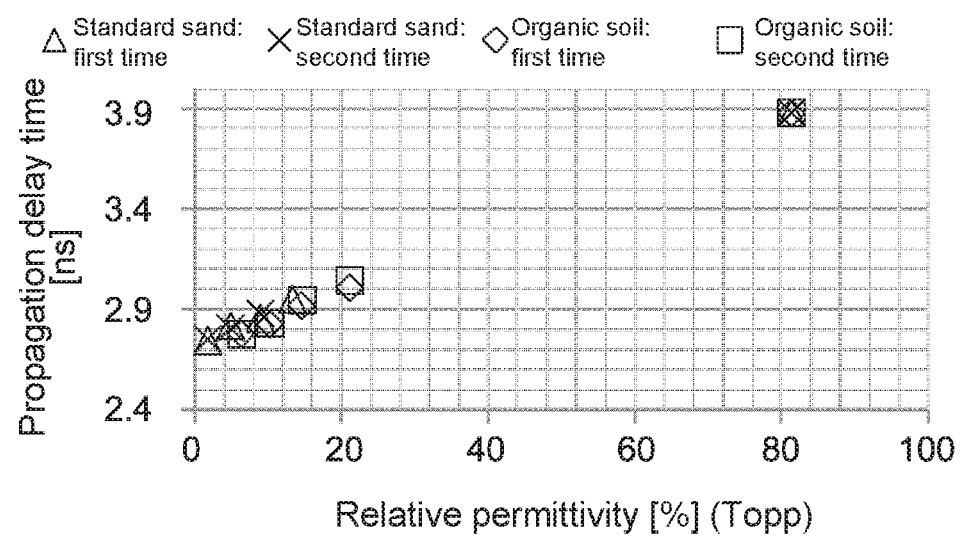
FIG. 16 is a diagram explaining an effect provided by the water amount measurement device.

As in the case of the first embodiment, FIGS. 15 and 16 respectively illustrate a graph plotted with the vertical axis representing a peak position of an impulse response (propagation delay time) and the horizontal axis representing water content by volume obtained by a soil sampling method, and a graph plotted with the vertical axis representing a peak position of an impulse response and the horizontal axis representing relative permittivity. Also in the present embodiment, an error was 1% or less for each time, and thus a gap had little impact.

Third Embodiment

Figure 17:
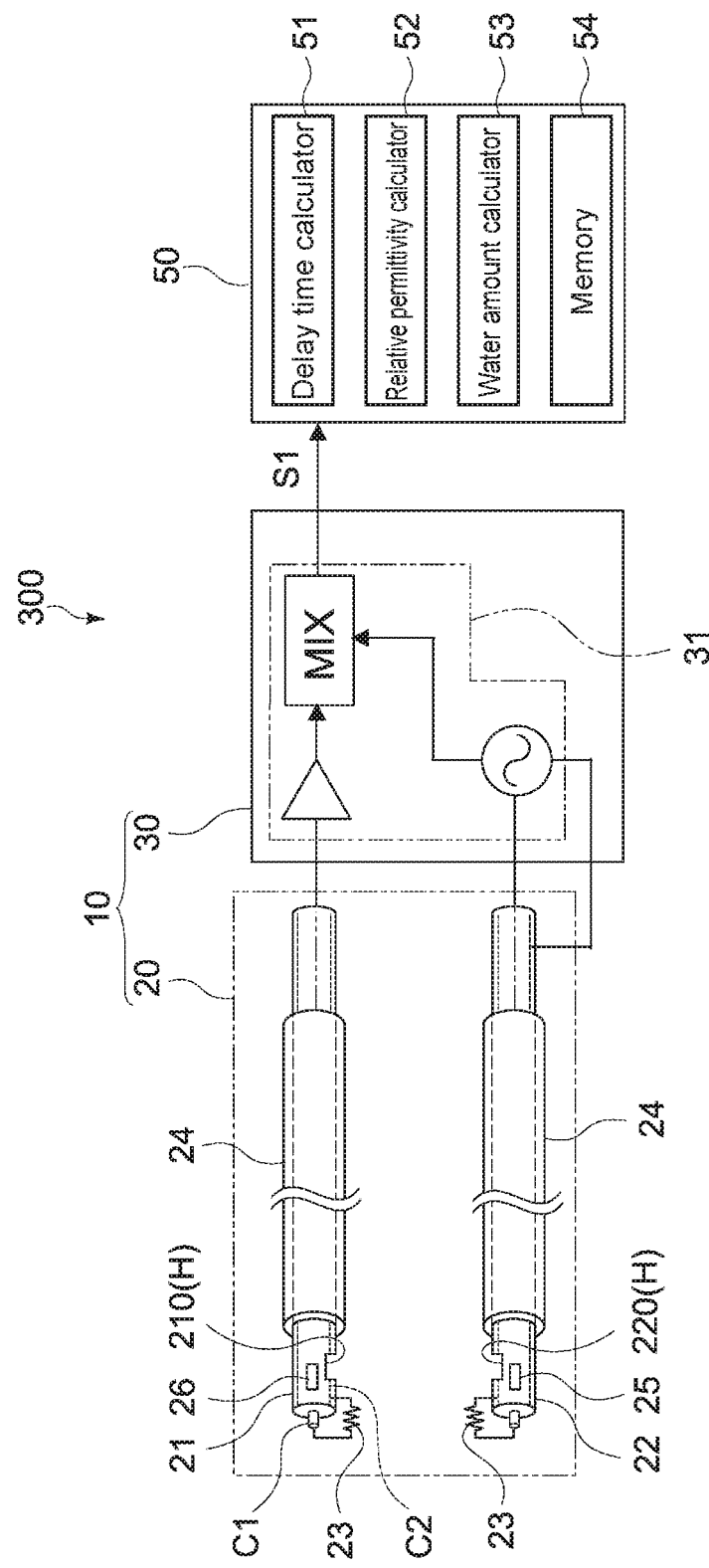
FIG. 17 schematically illustrates a configuration of a water amount measurement device that includes the sensor device according to a third embodiment of the present technology.

FIG. 17 schematically illustrates a configuration of a water amount measurement device according to a third embodiment of the present technology.

In the following descriptions, a component different from the first embodiment is primarily described, and the same component as the first embodiment is denoted by the same reference symbol and a description thereof is omitted or simplified.

A water amount measurement device 300 of the present embodiment is different from the water amount measurement device of the first embodiment in that the sensor head 20 includes a temperature detector 25 and an electric conductivity detector 26.

The temperature detector 25 is capable of detecting a temperature of the medium M. For example, an arbitrary temperature sensor such as a thermocouple or a thermistor can be adopted as the temperature detector 25.

The temperature detector 25 is provided in the vicinity of the antenna section 220 of the reception probe 22. Instead, the temperature detector 25 may be provided in a different position in the reception probe 22, such as the surface of the sleeve 24. The temperature detector 25 may be provided not only in the reception probe 22 but also in the transmission probe 21, or may be provided in the transmission probe 21.

The electric conductivity detector 26 is capable of detecting electric conductivity in the medium M. For example, an appropriate conductivity sensor or resistivity sensor of, for example, a two-wire type or a four-wire type, can be adopted as the electric conductivity detector 26.

The electric conductivity detector 26 is provided in the vicinity of the antenna section 210 of the transmission probe 21. Instead, the electric conductivity detector 26 may be provided in a different position in the transmission probe 21, such as the surface of the sleeve 24. The electric conductivity detector 25 may be provided not only in the transmission probe 21 but also in the reception probe 22, or may be provided in the reception probe 22.

It is known that the relative permittivity of a medium M has a fixed correlation with a temperature or electric conductivity of the medium M. The present embodiment makes it possible to obtain not only the characteristics of a propagation of an electromagnetic wave in a medium M but also information regarding a temperature and electric conductivity of the medium M, and thus, it is possible to correct a calculated value of the relative permittivity of the medium M or the volume content in the medium M according to the obtained temperature information or the obtained electric conductivity information. This makes it possible to further improve measurement accuracy.

In the present embodiment, the temperature detector 25 and the electric conductivity detector 26 are both provided in the sensor head 20. However, the configuration is not limited to this, and only one of them may be provided. Further, the end resistance 23 may be omitted as necessary. Instead of, or in addition to the temperature detector 25 and the electric conductivity detector 26, a pH detector that is capable of measuring a pH of a medium M may be provided in the sensor head 20.

Fourth Embodiment

Figure 18:
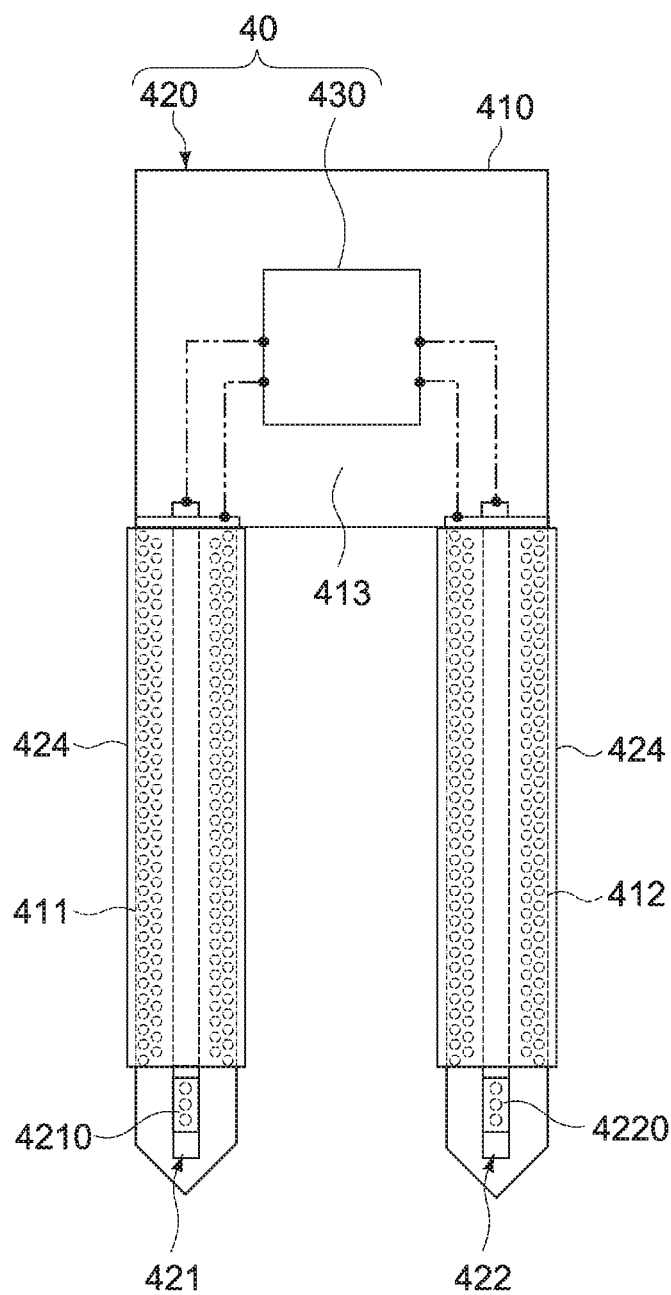
FIG. 18 is a front view schematically illustrating a configuration of a sensor device according to a fourth embodiment of the present technology.
Figure 19:
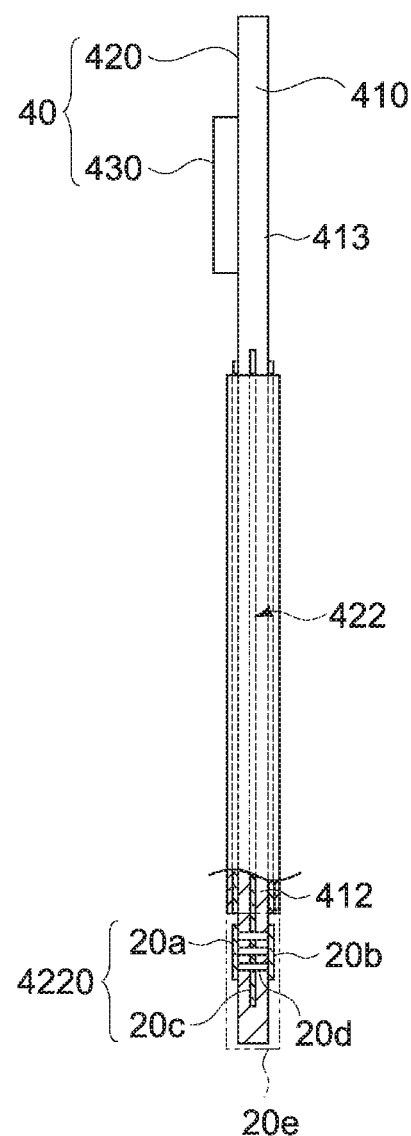
FIG. 19 is a partial-cutaway side view schematically illustrating the configuration of the sensor device according to the fourth embodiment of the present technology.

FIG. 18 and FIG. 19 are respectively a front view and a partial-cutaway side view that schematically illustrate a configuration of a sensor device according to another embodiment of the present technology. A sensor device 40 of the present embodiment includes a sensor head 420 and a measurement unit 430.

The sensor head 420 includes a support substrate 410, a transmission probe 421 (a first probe), and a reception probe 422 (a second probe). The support substrate 410 includes a first arm 411, a second arm 412, and a coupling portion 413. The transmission probe 421 is provided in the first arm 411, and the reception probe 422 is provided in the second arm 412.

The support substrate 410 is constituted of a plate material of a specified thickness, and is typically constituted of a wiring substrate including wiring layers on its surface and in the interior. The first and second arms 411 and 412 are each formed to have a strip shape having a specified length and extending in parallel with an axial direction, the strip shapes of the first and second arms 411 and 412 being situated at a specified distance from each other (for example, 20 mm to 100 mm). The coupling portion 413 is formed to be generally rectangular, and couples an end of the first arm 411 to an end of the second arm 412.

The transmission probe 421 and the reception probe 422 are each constituted of a stripline that includes surface layers 20a and 20b and an internal layer 20c. In the transmission probe 421 and the reception probe 422, the wiring layer constituting the internal layer 20c corresponds to a signal line, and the wiring layers constituting the surface layers 20a and 20b correspond to shield lines. The surface layers 20a and 20b and the internal layer 20c are typically constituted of copper foil.

The sensor head 420 further includes a pair of sleeves 424 each containing an electromagnetic wave absorption material. The sleeves 424 respectively cover a region of the transmission probe 421 of the first arms 411 and a region of the reception probe 422 of the second arms 412, the regions being regions except for tips (ends) of the first arms 411 and the second arms 412. In FIG. 18, peripheries of the first and second arms 411 and 412 each wrapped with the sleeve 424, are each provided with a plurality of openings, but these openings may be omitted.

The tips (ends) of the probes 421 and 422 that are each not wrapped with the sleeve 424, respectively constitute antenna sections 4210 and 4220 (a first antenna section and a second antenna section) of the probes 421 and 422. In the antenna sections 4210 and 4220, the surface layers 20a and 20b are electrically connected to each other through a single through-hole 20d or a plurality of through-holes 20d. The through-hole 20d may be hollow, or may be filled with resin material or metallic material. Alternatively, an end resistance may be connected instead of the through-hole 20. The antenna sections 4210 and 4220 may be covered with an electromagnetic-wave-permeability protection member 20e (FIG. 19).

The antenna sections 4210 and 4220 of the transmission probe 421 and the reception probe 422 are arranged to face each other, and are capable of transmitting and receiving an electromagnetic wave of a specified frequency between the two probes 421 and 422 embedded in a medium.

The measurement unit 430 corresponds to the measurement unit 30 of the first embodiment, and generates a measurement signal that includes information regarding the characteristics of a propagation of an electromagnetic wave in a medium between the antenna sections 4210 of the transmission probe 421 and the reception probe 422 of the reception probe 422.

The measurement unit 430 is integral with the sensor head 420. In the present embodiment, the measurement unit 430 is constituted of a single electronic component or a plurality of electronic components mounted on the surface of the coupling portion 413 of the support substrate 410. Through the wiring layers of the support substrate 410, the measurement unit 430 is electrically connected to the surface layers 20a and 20b and the internal layer 20c of the reception probe 421, and to the surface layers 20a and 20b and the internal layer 20c of the transmission probe 422.

The sensor device 40 of the present embodiment having the configuration described above also makes it possible to obtain an effect similar to that provided by the first embodiment described above. According to the present embodiment, the transmission probe 421 and the reception probe 422 are each constituted of a stripline, the striplines constituting the transmission probe 421 and the reception probe 422 being respectively provided in the first arm 411 and the second arm 412 of the support substrate 410, and this makes it possible to obtain a simple and tough configuration of the sensor head 420. According to the present embodiment, a certain distance is constantly maintained between the antenna sections 4210 and 4220, and this makes it possible to easily perform embedding in soil without adjusting the distance between the reception probe 421 and the transmission probe 422, and to improve the handleability.

In the present embodiment, the reception probe 421 and the transmission probe 422 are each constituted of a stripline. However, the configuration is not limited to this, and the reception probe 421 and the transmission probe 422 may be each constituted of a microstripline in which one of the surface layers 20a and 20b is omitted.

One of the first and second arms 411 and 412 of the support substrate 410 may be further provided with, for example, a temperature detector that detects a temperature of a medium, an electric conductivity detector that detects electric conductivity of a medium, and a pH detector that detects a pH of a medium.

<Modification>

Although the embodiments of the present technology have been described above, it is needless to say that the present technology is not limited only to the embodiments described above and various modifications may be made thereto.

For example, in the embodiments described above, the example of applying the present technology to the measurement of a water amount in soil where crops will grow, has been described. However, the present technology is not limited to this example, and it is also applicable to the measurement of the concentration of a different substance (such as fertilizer) whose relative permittivity is known.

The measurement target medium is not limited to soil, and may be a substance other than soil, such as livestock feed.

The water amount measurement device 100 is configured to calculate relative permittivity using the characteristics of a propagation of an electromagnetic wave in a medium, and to calculate a water amount in the medium using the relative permittivity. However, the configuration is not limited to this, and the water amount measurement device 100 may be configured to directly calculate a water amount in the medium using the obtained characteristics of a propagation of an electromagnetic wave. For example, when the medium is constituted of a relatively simple system, it is possible to create a correspondence table of the characteristics of a propagation of an electromagnetic wave and a water amount in the medium, and thus it is possible to directly obtain a water amount in the medium from the characteristics of a propagation of an electromagnetic wave by referring to the correspondence table.

In the embodiments described above, the example in which the signal processing unit 50 is constituted of a single information processing device, has been described. However, the configuration is not limited to this, and the signal processing unit 50 may be constituted of a computer system in which a plurality of computers operates in conjunction with one another.

Further, each of the embodiments described above has been described using the example in which a transmission probe and a reception probe in a sensor device each include a single antenna section. However, the configuration is not limited to this, and at least one of a transmission probe or a reception probe may include a plurality of antenna sections. Moreover, the configuration of a sensor device is not limited to the example of including a single transmission probe and a single reception probe, and the sensor device may include at least one of a plurality of transmission probes or a plurality of reception probes.

Figure 20:
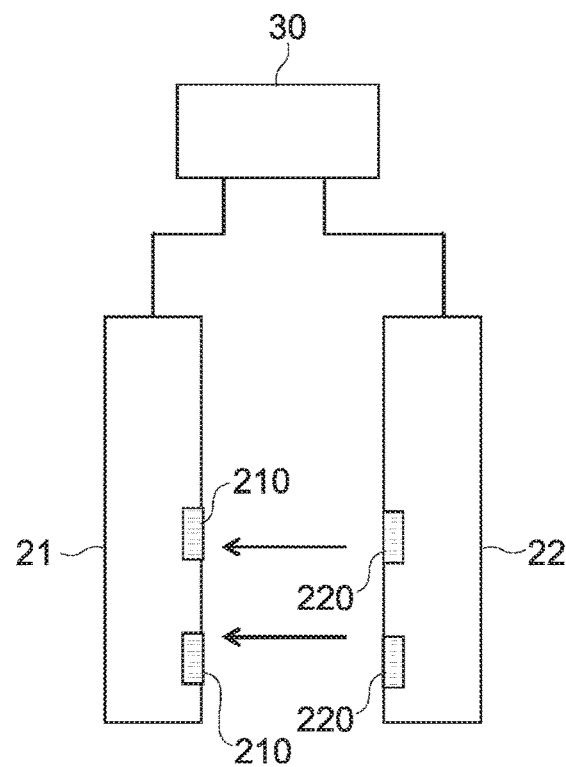
FIG. 20 schematically illustrates a configuration of a modification of the sensor device according to the embodiments of the present technology.

For example, a sensor device illustrated in FIG. 20 includes the antenna sections 210 and 220 that respectively include two transmission probes 21 and two reception probes 22. In this example, the antenna section 210 of the transmission probe 21 and the antenna section 220 of the reception probe 22 are arranged to be situated at a specified distance from each other in parallel with an axial direction of the two probes 21 and 22, and to face each other.

Figure 21:
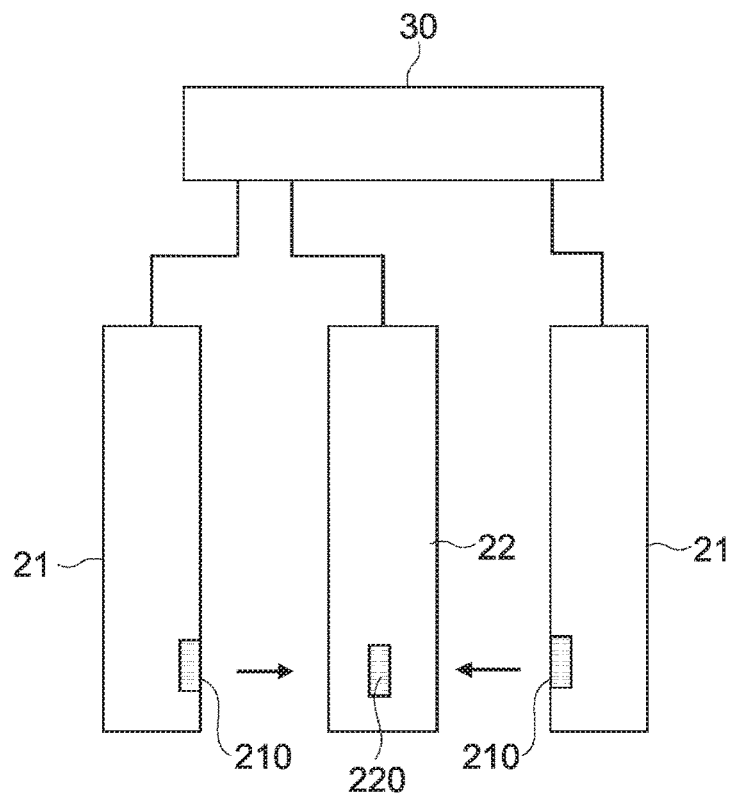
FIG. 21 schematically illustrates a configuration of a modification of the sensor device according to the embodiments of the present technology.

A sensor device illustrated in FIG. 21 includes two transmission probes 21 and one reception probe, and the transmission probe 21 and the reception probe 22 respectively include one antenna section 210 and one antenna section 220. In this example, the reception probe 22 is arranged between the two transmission probes 21, and the configuration is made such that an electromagnetic wave is transmitted from the antenna section 210 of each transmission probe 21 to the antenna section 220 of the reception probe 22.

Figure 22:
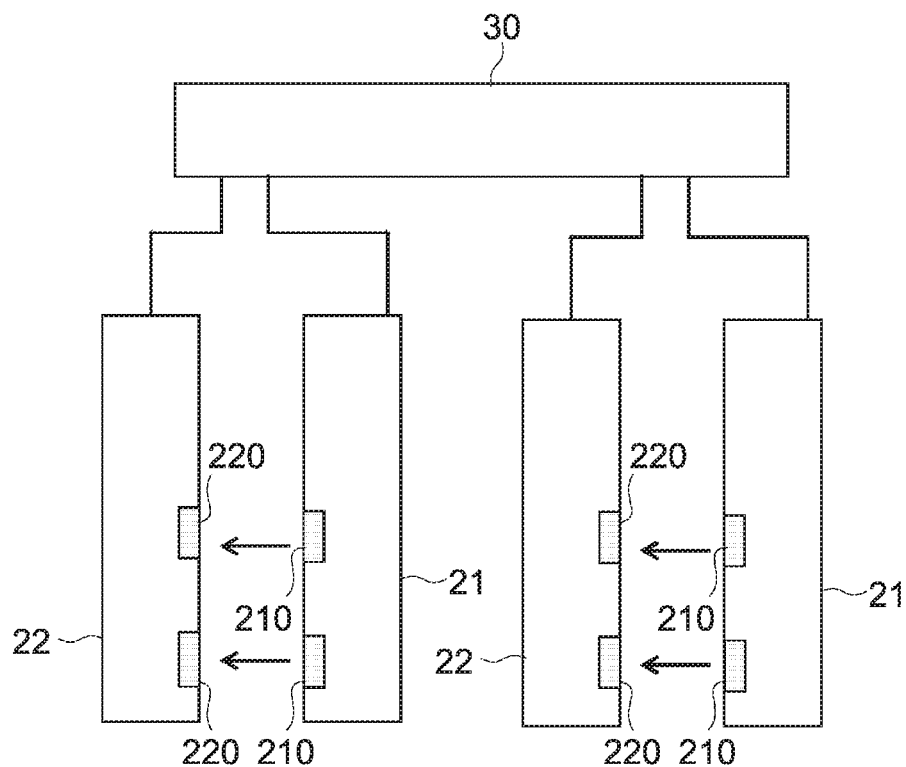
FIG. 22 schematically illustrates a configuration of a modification of the sensor device according to the embodiments of the present technology.

A sensor device illustrated in FIG. 22 includes two transmission probes 21 and two reception probes 22, and each transmission probe 21 and a corresponding one of the reception probes 22 are arranged to face each other in pairs. In this example, the transmission probe 21 and the reception probe 22 respectively include two antenna sections 210 and two antenna sections 220, as illustrated in FIG. 20. However, the configuration is not limited to this, and a state in which the probes 21 and 22 respectively include one antenna section 210 and one antenna section 220, is also applicable.

Figure 23:
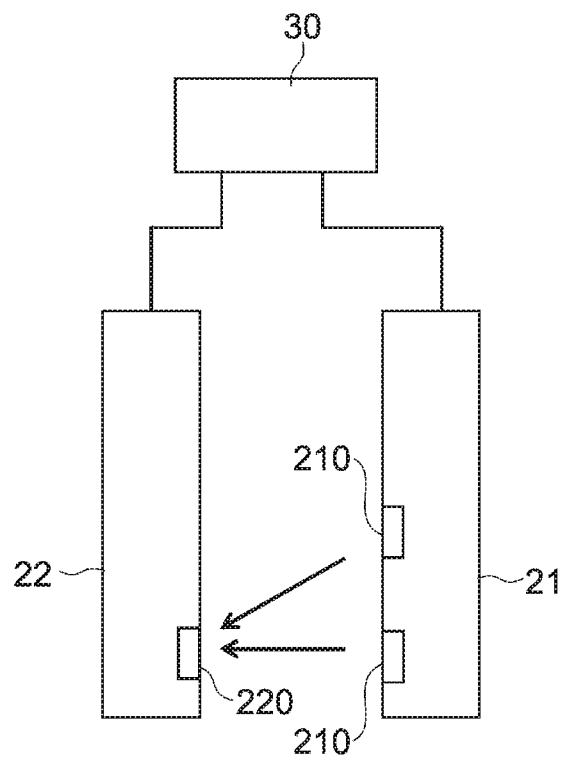
FIG. 23 schematically illustrates a configuration of a modification of the sensor device according to the embodiments of the present technology.

A sensor device illustrated in FIG. 23 includes the transmission probe 21 including two antenna sections 210, and the reception probe 22 including one antenna section 220, and the antenna section 220 of the reception probe 22 is capable of receiving an electromagnetic wave transmitted from each antenna section 210 of the transmission probe 21.

Figure 24:
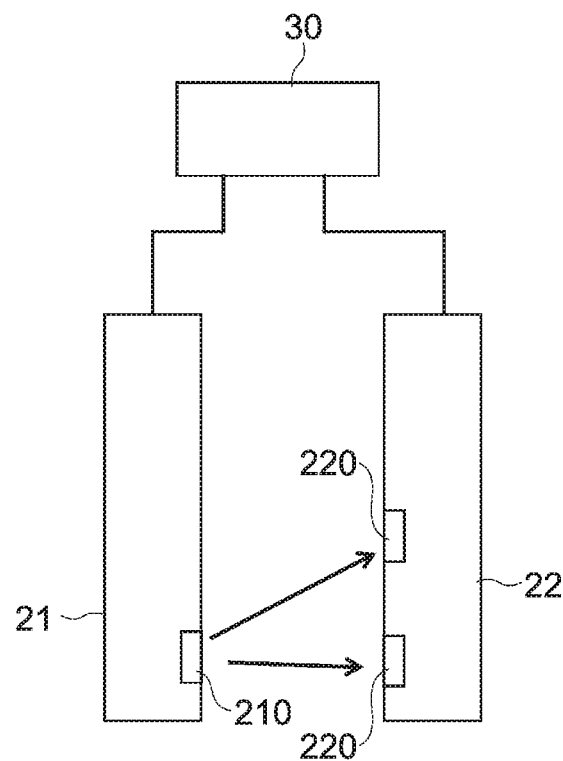
FIG. 24 schematically illustrates a configuration of a modification of the sensor device according to the embodiments of the present technology.

A sensor device illustrated in FIG. 24 includes the transmission probe 21 including one antenna section 210, and the reception probe 22 including two antenna sections 220, and the antenna section 210 of the transmission probe 21 is capable of transmitting an electromagnetic wave to each antenna section 220 of the reception probe 22.

Figure 25:
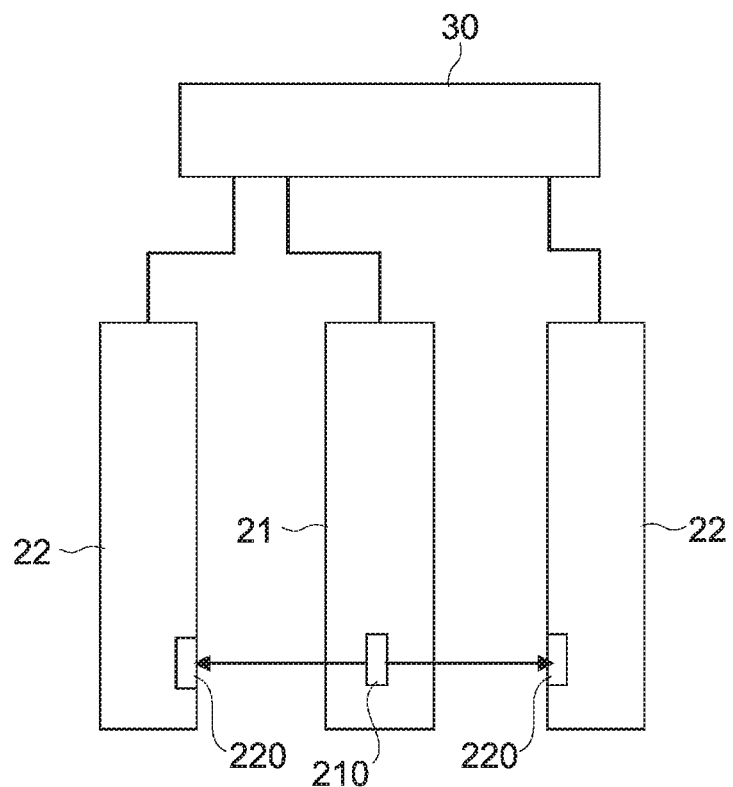
FIG. 25 schematically illustrates a configuration of a modification of the sensor device according to the embodiments of the present technology.

A sensor device illustrated in FIG. 25 includes one transmission probe 21 and two reception probes 22, and the transmission probe 21 and the reception probe 22 respectively include one antenna section 210 and one antenna section 220. In this example, the transmission probe 21 is arranged between the two reception probes 22, and the antenna sections 220 of the respective reception probes 22 are each capable of receiving an electromagnetic wave transmitted from the antenna section 210 of the transmission probe 21.

Figure 26:
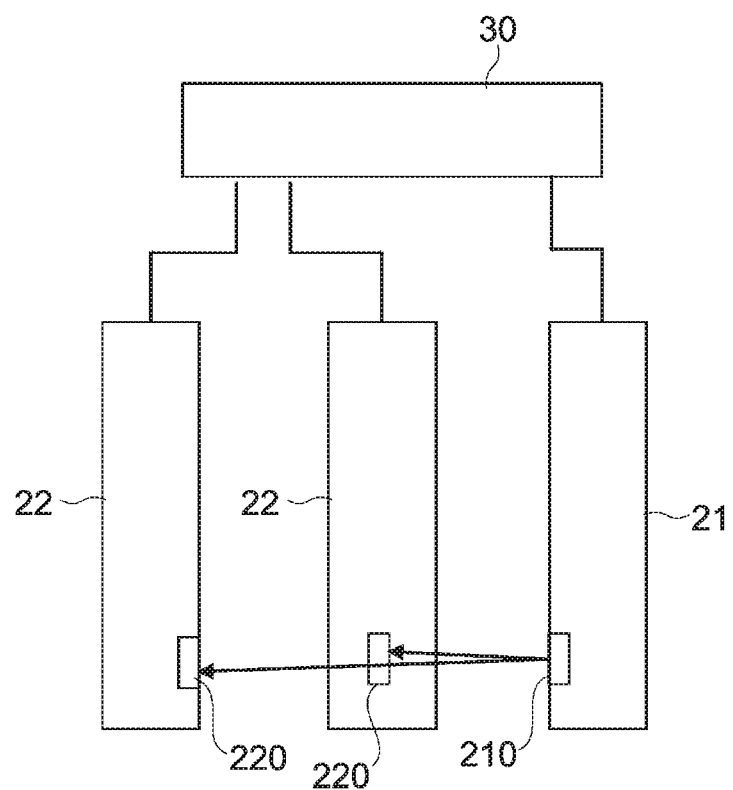
FIG. 26 schematically illustrates a configuration of a modification of the sensor device according to the embodiments of the present technology.

A sensor device illustrated in FIG. 26 includes one transmission probe 21 and two reception probes 22, and the transmission probe 21 and the reception probe 22 respectively include one antenna section 210 and one antenna section 220. Also in this example, the antenna sections 220 of the respective reception probes 22 are each capable of receiving an electromagnetic wave transmitted from the antenna section 210 of the transmission probe 21, and the antenna sections 220 of the respective reception probes 22 are arranged at different distances from the antenna section 210 of the transmission probe 21.

Note that the present technology may also take the following configurations.

(1) A sensor device including:
a sensor head that includes a first probe and a second probe, the first probe including a first antenna section used for transmission, the second probe including a second antenna section used for reception, the second probe being situated at a specified distance from the first probe and facing the first probe; and
a measurement unit that includes a signal generator that generates a measurement signal that includes information regarding characteristics of a propagation of an electromagnetic wave in a medium between the first and second antenna sections.

(2) The sensor device according to (1), in which
the first and second probes are each constituted of a coaxial cable that includes a core wire portion and a shield portion, and
the first and second antenna sections each include a hole provided in a portion of the shield portion.

(3) The sensor device according to (2), in which
the first and second probes each include an end resistance that is electrically connected between an end of the core wire portion and the shield portion.

(4) The sensor device according to (2) or (3), in which
the sensor head further includes an electromagnetic wave absorption material that is provided in each of the first and second probes to cover a portion around the hole in the shield portion.

(5) The sensor device according to (4), in which
the electromagnetic wave absorption material includes ferrite.

(6) The sensor device according to (1), in which
the sensor head further includes a support substrate that includes a first arm, a second arm, and a coupling portion that couples the first arm to the second arm, and
the first and second probes are respectively constituted of striplines respectively provided in the first and second arms.

(7) The sensor device according to (6), in which
the measurement unit is mounted on the coupling portion.

(8) The sensor device according to any one of (1) to (7), in which
the sensor head further includes a temperature detector that is provided in at least one of the first probe or the second probe and is capable of detecting a temperature of the medium.

(9) The sensor device according to any one of (1) to (8), in which
the sensor head further includes an electric conductivity detector that is provided in at least one of the first probe or the second probe and is capable of detecting electric conductivity of the medium.

(10) The sensor device according to any one of (1) to (9), in which
the signal generator includes a signal creating section that inputs a pulse signal of a specified frequency to the first probe, and a quadrature detector that performs quadrature detection on an output from the second probe.

(11) The sensor device according to any one of (1) to (10), in which
the measurement unit further includes a communication section that is capable of transmitting the measurement signal to an information processing device.

(12) A water amount measurement device including:
a sensor head that includes a first probe and a second probe, the first probe including a first antenna section used for transmission, the second probe including a second antenna section used for reception, the second probe being situated at a specified distance from the first probe and facing the first probe;
a measurement unit that generates a measurement signal that includes information regarding characteristics of a propagation of an electromagnetic wave in a medium between the first and second antenna sections; and
a signal processing unit that measures a water amount in the medium using the measurement signal.

(13) The water amount measurement device according to (12), in which
the signal processing unit includes
a delay time calculator that calculates a propagation delay time of an electromagnetic wave between the first and second probes using the measurement signal,
a relative permittivity calculator that calculates relative permittivity of a medium using the propagation delay time, and
a water amount calculator that calculates a water amount in the medium using the relative permittivity.

(14) The water amount measurement device according to (12) or (13), in which
the sensor head further includes a temperature detector that is capable of detecting a temperature of the medium, and
the signal processing unit corrects the water amount according to an output from the temperature detector.

(15) The water amount measurement device according to any one of (12) to (14), in which
the sensor head further includes an electric conductivity detector that is capable of detecting electric conductivity of the medium, and
the signal processing unit corrects the water amount according to an output from the electric conductivity detector.

(16) A water amount measurement method including:
receiving, by a second antenna section of a second probe, an electromagnetic wave transmitted from a first antenna section of a first probe arranged in a medium, and generating a measurement signal that includes information regarding characteristics of a propagation of the electromagnetic wave, the second probe being arranged in the medium to be situated at a specified distance from the first probe, and
measuring a water amount in the medium using the measurement signal.

(17) The water amount measurement method according to (16), in which
the measuring the water amount includes
calculating a propagation delay time of the electromagnetic wave that is measured using the measurement signal,
calculating relative permittivity of the medium using the propagation delay time, and
calculating a water amount in the medium using the relative permittivity.

(18) The water amount measurement method according to (16) or (17), in which
the medium is soil.

(19) An information processing device including:
a delay time calculator that calculates a propagation delay time of an electromagnetic wave between a first probe and a second probe using an electromagnetic wave transmitted from a first antenna section of the first probe and received by a second antenna section of the second probe, the first probe being arranged in a medium, the second probe being arranged in the medium to be situated at a specified distance from the first probe;
a relative permittivity calculator that calculates relative permittivity of the medium using the propagation delay time; and
a water amount calculator that calculates a water amount in the medium using the relative permittivity.

(20) An information processing method including:
calculating a propagation delay time of an electromagnetic wave between a first probe and a second probe using an electromagnetic wave transmitted from a first antenna section of the first probe and received by a second antenna section of the second probe, the first probe being arranged in a medium, the second probe being arranged in the medium to be situated at a specified distance from the first probe;
calculating relative permittivity of the medium using the propagation delay time; and
calculating a water amount in the medium using the relative permittivity.

REFERENCE SIGNS LIST 10, 40 sensor device
20, 420 sensor head
21, 421 transmission probe
22, 422 reception probe
23 end resistance
24, 424 sleeve
25 temperature detector
26 electric conductivity detector
30, 430 measurement unit
31 signal generator
32 communication section
50 signal processing unit
51 delay time calculator
52 relative permittivity calculator
53 water amount calculator
100, 200, 300 water amount measurement device
210, 220, 4210, 4220 antenna section
310 controller
311 signal creating section
313 phase shifter
314 mixer

The invention claimed is:

1. A sensor device, comprising:
a sensor head that includes a first probe and a second probe, the first probe including a first antenna section used for transmission, the second probe including a second antenna section used for reception, the second probe being situated at a specified distance from the first probe and facing, the first probe; and
a measurement unit that includes a signal generator that generates a measurement signal that includes information regarding characteristics of a propagation of an electromagnetic wave in a medium between the first and second antenna sections,
wherein the first and second probes are each constituted of a coaxial cable that includes a core wire portion and a shield portion, and
wherein the first and second antenna sections each include a hole provided in a portion of the shield portion, and
wherein the sensor head further includes an electromagnetic wave absorption material that is provided in each of the first and second probes to cover a portion around the hole in the shield portion.

2. The sensor device according to claim 1, wherein the electromagnetic wave absorption material includes ferrite.

3. The sensor device according to claim 1, wherein the measurement unit further includes a communication section that is capable of transmitting the measurement signal to an information processing device.

4. The sensor device according to claim 1, wherein the first and second probes each include an end resistance that is electrically connected between an end of the core wire portion and the shield portion.

5. The sensor device according to claim 1, wherein the sensor head further includes a temperature detector that is provided in at least one of the first probe or the second probe and is capable of detecting a temperature of the medium.

6. The sensor device according to claim 1, wherein the sensor head further includes an electric conductivity detector that is provided in at least one of the first probe or the second probe and is capable of detecting electric conductivity of the medium.

7. The sensor device according to claim 1, wherein the signal generator includes a signal creating section that inputs a pulse signal of a specified frequency to the first probe, and a quadrature detector that performs quadrature detection on an output from the second probe.

8. The sensor device according to claim 1, wherein the measurement unit further includes a communication section that is capable of transmitting the measurement signal to an information processing device.

9. A sensor device, comprising:
a sensor head that includes a first probe and a second probe, the first probe including a first antenna section used for transmission the second robe including a second antenna section used for reception, the second probe being situated at a specified distance from the first probe and facing the first probe; and
a measurement unit that includes a signal generator that generates a measurement signal that includes information regarding characteristics of a propagation of an electromagnetic wave in a medium between the first and second antenna sections,
wherein the sensor head further includes a support substrate that includes a first arm, a second arm, and a coupling portion that couples the first arm to the second arm, and wherein the first and second probes are respectively constituted of striplines respectively provided in the first and second arms.

10. The sensor device according to claim 9, wherein the measurement unit is mounted on the coupling portion.

11. A sensor device, comprising:
a sensor head that includes a first probe and a second probe, the first probe including a first antenna section used for transmission the second robe including a second antenna section used for reception, the second probe being situated at a specified distance from the first probe and facing the first probe; and
a measurement unit that includes a signal generator that generates a measurement signal that includes information regarding characteristics of a propagation of an electromagnetic wave in a medium between the first and second antenna sections,
wherein the sensor head further includes a temperature detector that is provided in at least one of the first probe or the second probe and is capable of detecting a temperature of the medium.

12. The sensor device according to claim 11, wherein
the first and second probes are each constituted of a coaxial cable that includes a core wire portion and a shield portion, and
the first and second antenna sections each include a hole provided in a portion of the shield portion.

13. The sensor device according to claim 12, wherein
the first and second probes each include an end resistance that is electrically connected between an end of the core wire portion and the shield portion.

14. The sensor device according to claim 11, wherein the sensor head further includes an electric conductivity detector that is provided in at least one of the first probe or the second probe and is capable of detecting electric conductivity of the medium.

15. The sensor device according to claim 11, wherein the signal generator includes a signal creating section that inputs a pulse signal of a specified frequency to the first probe, and a quadrature detector that performs quadrature detection on an output from the second probe.

16. The sensor device according to claim 11, wherein the measurement unit further includes a communication section that is capable of transmitting the measurement signal to an information processing device.

17. A sensor device, comprising:
a sensor head that includes a first robe and a second probe, the first robe including a first antenna section used for transmission, the second probe including a second antenna section used for reception, the second probe being situated at a specified distance from the first probe and facing the first probe; and
a measurement unit that includes a signal generator that generates a measurement signal that includes information regarding characteristics of a propagation of an electromagnetic wave in a medium between the first and second antenna sections,
wherein the sensor head further includes an electric conductivity detector that is provided in at least one of the first probe or the second probe and is capable of detecting electric conductivity of the medium.

18. A sensor device, comprising:
a sensor head that includes a first probe and a second probe, the first probe including a first antenna section used for transmission, the second probe including a second antenna section used for reception, the second probe being situated at a specified distance from the first probe and facing the first probe; and
a measurement unit that includes a signal generator that generates a measurement signal that includes information regarding characteristics of a propagation of an electromagnetic wave in a medium between the first and second antenna section,
wherein the signal generator includes a signal creating section that inputs a pulse signal of a specified frequency to the first probe, and a quadrature detector that performs quadrature detection on an output from the second probe.

19. A water amount measurement device, comprising:
a sensor head that includes a first probe and a second probe the first probe including a first antenna section used for transmission, the second probe including a second antenna section used for reception, the second probe being situated at a specified distance from the first probe and facing the first probe;
a measurement unit that generates a measurement signal that includes information regarding characteristics of a propagation of an electromagnetic wave in a medium between the first and second antenna sections; and
a signal processing unit that measures a water amount in the medium using the measurement signal,
wherein the sensor head further includes a temperature detector that is capable of detecting a temperature of the medium, and
wherein the signal processing unit corrects the water amount according to an output from the temperature detector.

20. The water amount measurement device according to claim 19, wherein
the signal processing unit includes
a delay time calculator that calculates a propagation delay time of an electromagnetic wave between the first and second probes using the measurement signal,
a relative permittivity calculator that calculates relative permittivity of a medium using the propagation delay time, and
a water amount calculator that calculates a water amount in the medium using the relative permittivity.

21. A water amount measurement device, comprising:
including a first antenna section used for transmission, the second probe including a second antenna section used for reception, the second probe being situated at a specified distance from the first probe and facing the first probe;
a measurement unit that generates a measurement signal that includes information regarding characteristics of a propagation of an electromagnetic wave in a medium between the first and second antenna sections; and
a signal processing unit that measures a water amount in the medium using the measurement signal,
wherein the sensor head further includes an electric conductivity detector that is capable of detecting electric conductivity of the medium, and
wherein the signal processing unit corrects the water amount according to an output from the electric conductivity detector.

* * * * *